United States Patent

Lin et al.

(10) Patent No.: US 9,359,339 B2
(45) Date of Patent: Jun. 7, 2016

(54) GLUCAGON RECEPTOR ANTAGONIST COMPOUNDS, COMPOSITIONS CONTAINING SUCH COMPOUNDS AND METHODS OF USE

(71) Applicant: Merck Sharp & Dohme Corp., Rahway, NJ (US)

(72) Inventors: Songnian Lin, Monroe, NJ (US); Fengqi Zhang, Edison, NJ (US); Emma R. Parmee, Doylestown, PA (US); Sunita V. Dewnani, Secaucus, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/452,143

(22) Filed: Aug. 5, 2014

(65) Prior Publication Data

US 2015/0018399 A1     Jan. 15, 2015

Related U.S. Application Data

(63) Continuation of application No. 13/146,220, filed as application No. PCT/US2010/021098 on Jan. 15, 2010, now abandoned.

(60) Provisional application No. 61/206,142, filed on Jan. 28, 2009.

(51) Int. Cl.
| | |
|---|---|
| C07D 413/12 | (2006.01) |
| C07D 333/24 | (2006.01) |
| C07D 409/12 | (2006.01) |
| C07D 413/04 | (2006.01) |
| C07D 333/60 | (2006.01) |
| C07D 409/04 | (2006.01) |

(52) U.S. Cl.
CPC ............ *C07D 413/12* (2013.01); *C07D 333/24* (2013.01); *C07D 333/60* (2013.01); *C07D 409/04* (2013.01); *C07D 409/12* (2013.01); *C07D 413/04* (2013.01)

(58) Field of Classification Search
None
See application file for complete search history.

(56) References Cited

U.S. PATENT DOCUMENTS

| | | | | |
|---|---|---|---|---|
| 6,762,318 | B2 * | 7/2004 | Kodra et al. .................. | 562/445 |
| 2003/0109570 | A1 | 6/2003 | Tsunoda et al. | |
| 2008/0085926 | A1 * | 4/2008 | Stelmach et al. ............. | 514/415 |
| 2008/0125468 | A1 * | 5/2008 | Chappell et al. .............. | 514/357 |

FOREIGN PATENT DOCUMENTS

| | | |
|---|---|---|
| WO | 00/69810 A1 | 11/2000 |
| WO | 03/048109 A1 | 6/2003 |
| WO | 2006/102067 A1 | 9/2006 |
| WO | 2008/042223 A1 | 4/2008 |
| WO | 2008/098244 A1 | 8/2008 |
| WO | 2010/030722 A1 | 3/2010 |
| WO | 2010/071750 A1 | 6/2010 |

OTHER PUBLICATIONS

Chung et al. (Diastereoselective Friedel—Crafts Alkylation of Indoles with Chiral α-Phenyl Benzylic Cations. Asymmetric Synthesis of Anti-1,1,2-Triarylalkanes. Org Lett. Jul. 17, 2008;10(14):3037-40. Epub Jun. 19, 2008.*
International Search Report of PCT/US2010/021098, mailed Mar. 2, 2012.
International Preliminary Report on Patentability of PCT/US2010/021098, issued Aug. 2, 2011.

* cited by examiner

*Primary Examiner* — Maury Audet
(74) *Attorney, Agent, or Firm* — Anna L. Cocuzzo; Catherine D. Fitch

(57) ABSTRACT

Glucagon receptor antagonist compounds are disclosed. The compounds are useful for treating type 2 diabetes and related conditions. Pharmaceutical compositions and methods of treatment are also included.

20 Claims, No Drawings

GLUCAGON RECEPTOR ANTAGONIST COMPOUNDS, COMPOSITIONS CONTAINING SUCH COMPOUNDS AND METHODS OF USE

BACKGROUND OF THE INVENTION

The present invention relates to glucagon receptor antagonist compounds, compositions containing such compounds and various methods of treatment relating to type 2 diabetes mellitus and related conditions.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level >126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure >130/80 mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by alpha cells in pancreatic islets in response to falling blood glucose levels. The hormone binds to specific receptors in liver cells that trigger glycogenolysis and an increase in gluconeogenesis through cAMP-mediated events. These responses generate glucose (e.g. hepatic glucose production) to help maintain euglycemia by preventing blood glucose levels from falling significantly. In addition to elevated levels of circulating insulin, type 2 diabetics have elevated levels of plasma glucagon and increased rates of hepatic glucose production. Antagonists of the glucagon receptor are useful in improving insulin responsiveness in the liver, decreasing the rate of gluconeogenesis and glycogenolysis, and lowering the rate of hepatic glucose output resulting in a decrease in the levels of plasma glucose.

SUMMARY OF THE INVENTION

The present invention relates to a compound represented by formula I:

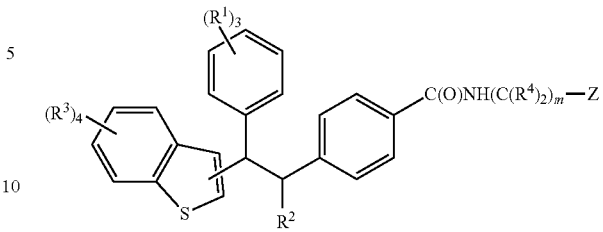

or a pharmaceutically acceptable salt or solvate thereof wherein:

each $R^1$ represents H or is selected from the group consisting of halo, CN, OH, $NO_2$, $CO_2R^a$, $NR^aR^b$, $S(O)_pR^a$, $C_{1-10}$alkyl, $C_{2-10}$alkenyl or $C_{1-10}$alkoxy, the alkyl and alkenyl portions of $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo and $C_{1-6}$alkoxy;

p represents 0, 1 or 2;

each $R^a$ and $R^b$ independently represents H or $C_{1-4}$alkyl optionally substituted with 1-5 halo atoms up to perhalo; and further optionally substituted with 1 group selected from OH, oxo and $C_{1-6}$alkoxy;

$R^2$ represents $C_{1-6}$alkyl or $C_{2-6}$alkenyl, each optionally substituted with 1-5 halo atoms up to perhalo, and further optionally substituted with 1 group selected from OH, oxo and $C_{1-6}$alkoxy;

each $R^3$ represents H or is selected from the group consisting of halo; CN; OH; $NO_2$; $CO_2R^a$; $NR^aR^b$; $S(O)_pR^a$; a 5-membered heteroaryl ring containing 1-3 nitrogen atoms, 0-1 oxygen or sulfur atom, and optionally substituted with 1-2 $C_{1-4}$alkyl groups; $C_{1-10}$alkyl; $C_{2-10}$alkenyl and $C_{1-10}$alkoxy, the alkyl and alkenyl portions of $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo, $NR^aR^b$ and $C_{1-6}$alkoxy;

each $R^4$ independently represents H or is selected from the group consisting of halo, OH, $C_{1-4}$alkyl, $OC_{1-4}$alkyl, halo$C_{1-4}$alkyl and haloO$C_{1-4}$alkyl;

m represents 0, 1 or 2; such that when m represents 0 or 1, Z represents tetrazolyl; and when m represents 2, Z represents a member selected from the group consisting of $CO_2H$, $SO_3H$ and $C(O)NH_2$.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. Examples of cycloalkyl include cyclopropyl, cyclobutyl, cyclopentyl, cyclohexyl, cycloheptyl, decahydronaphthyl and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like. Cycloalkenyl is a subset of alkenyl. If no number is specified, 4-8 carbon atoms are included. Examples include cyclopentenyl, cyclohexenyl and the like.

"Aryl" (Ar) means mono- and bicyclic aromatic rings containing 6-12 carbon atoms. Examples of aryl include phenyl, naphthyl, indenyl and the like. "Aryl" also includes monocyclic rings fused to an aryl group. Examples include tetrahydronaphthyl, indanyl and the like.

"Heteroaryl" (HAR) means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Halogen" (Halo) includes fluorine, chlorine, bromine and iodine. Haloalkyl and haloalkoxy refer to halogenated alkyl and alkoxy groups having the indicated number of carbon atoms, substituted with one to five halo atoms, up to perhalo, and preferably one to three halo atoms selected from fluoro and chloro. Thus, for example, $haloC_{1-6}alkyl$ refers to a $C_{1-6}alkyl$ group substituted with halo atoms, up to perhalo.

Numbering around the benzothiophene is conventional, as shown below:

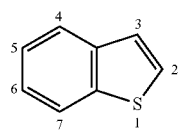

It is also noted that while structures I, I-1 and I-2 depict the $R^3$ groups on the benzene ring of the benzothiophene moiety, the $R^3$ groups can be attached at any available point on the thiophene portion as well.

One aspect of the invention relates to a compound represented by formula I:

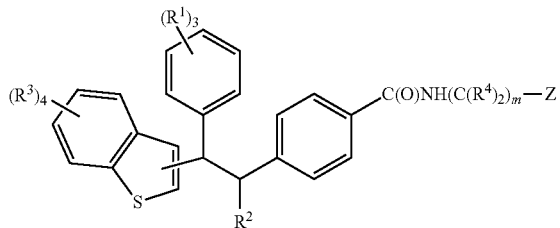

or a pharmaceutically acceptable salt or solvate thereof wherein:

each $R^1$ represents H or is selected from the group consisting of halo, CN, OH, $NO_2$, $CO_2R^a$, $NR^aR^b$, $S(O)_pR^a$, $C_{1-10}alkyl$, $C_{2-10}alkenyl$ or $C_{1-10}alkoxy$, the alkyl and alkenyl portions of $C_{1-10}alkyl$, $C_{2-10}alkenyl$ and $C_{1-10}alkoxy$ being optionally substituted with 1-5 halo atoms up to perhalo; and further optionally substituted with 1 group selected from OH, oxo and $C_{1-6}alkoxy$;

p represents 0, 1 or 2;

each $R^a$ and $R^b$ independently represents H or $C_{1-4}alkyl$ optionally substituted with 1-5 halo atoms up to perhalo; and further optionally substituted with 1 group selected from OH, oxo and $C_{1-6}alkoxy$;

$R^2$ represents $C_{1-6}alkyl$ or $C_{2-6}alkenyl$, each optionally substituted with 1-5 halo atoms up to perhalo, and further optionally substituted with 1 group selected from OH, oxo and $C_{1-6}alkoxy$;

each $R^3$ represents H or is selected from the group consisting of halo; CN; OH; $NO_2$; $CO_2R^a$; $NR^aR^b$; $S(O)_pR^a$; a 5-membered heteroaryl ring containing 1-3 nitrogen atoms, 0-1 oxygen or sulfur atom, and optionally substituted with 1-2 $C_{1-4}alkyl$ groups; $C_{1-10}alkyl$; $C_{2-10}alkenyl$ and $C_{1-10}alkoxy$, the alkyl and alkenyl portions of $C_{1-10}alkyl$, $C_{2-10}alkenyl$ and $C_{1-10}alkoxy$ being optionally substituted with 1-5 halo atoms up to perhalo; and further optionally substituted with 1 group selected from OH, oxo, $NR^aR^b$ and $C_{1-6}alkoxy$;

each $R^4$ independently represents H or is selected from the group consisting of halo, OH, $C_{1-4}alkyl$, $OC_{1-4}alkyl$, $haloC_{1-4}alkyl$ and $haloOC_{1-4}alkyl$;

m represents 0, 1 or 2; such that when m represents 0 or 1, Z represents tetrazolyl; and when m represents 2, Z represents a member selected from the group consisting of $CO_2H$, $SO_3H$ and $C(O)NH_2$.

An aspect of the invention that is of interest relates to a compound of formula I-1:

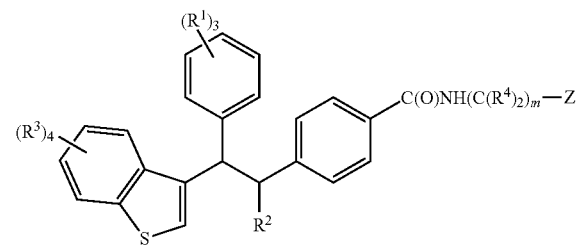

or a pharmaceutically acceptable salt or solvate thereof. The variables are as defined with respect to formula I.

Another aspect of the invention that is of interest relates to a compound of formula I-2:

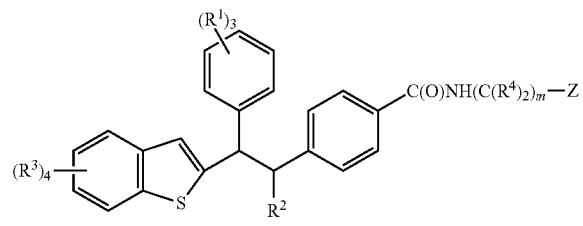

or a pharmaceutically acceptable salt or solvate thereof. The variables are as defined with respect to formula I.

Another aspect of the invention that is of interest relates to compounds in accordance with formula I or a pharmaceutically acceptable salt or solvate thereof wherein each $R^1$ represents H or is selected from the group consisting of halo, CN, $C_{1-6}$alkyl, $C_{1-6}$alkoxy, halo$C_{1-6}$alkyl and halo$C_{1-6}$alkoxy.

In particular, another aspect of the invention that is of interest relates to compounds in accordance with formula I or a pharmaceutically acceptable salt or solvate thereof wherein each $R^1$ represents H or is selected from the group consisting of: halo selected from fluoro and chloro; CN; $CH_3$; $OCH_3$; $CF_3$ and $OCF_3$.

Another aspect of the invention that is of interest relates to compounds in accordance with formula I or a pharmaceutically acceptable salt or solvate thereof wherein $R^2$ represents a member selected from the group consisting of: $C_{1-6}$alkyl and $C_{3-4}$alkenyl, each optionally substituted with 1-3 halo atoms.

In particular, another aspect of the invention that is of interest relates to compounds in accordance with formula I or a pharmaceutically acceptable salt or solvate thereof wherein $R^2$ represents $C_{2-5}$alkyl optionally substituted with 1-3 halo atoms.

Even more particularly, another aspect of the invention that is of interest relates to compounds in accordance with formula I or a pharmaceutically acceptable salt or solvate thereof wherein $R^2$ is selected from the group consisting of ethyl, n-propyl, isopropyl, n-butyl, isobutyl, sec-butyl and 3-methylbutyl, each optionally substituted with 1-3 halo atoms selected from fluoro and chloro.

Even more particularly, another aspect of the invention that is of interest relates to compounds in accordance with formula I or a pharmaceutically acceptable salt or solvate thereof wherein $R^2$ is selected from the group consisting of ethyl, n-propyl, n-butyl, $CH_2CH(CH_3)_2$, $CH_2CH_2CH(CH_3)_2$ and $CH_2CH_2CF_3$.

Another aspect of the invention that is of interest relates to compounds in accordance with formula I or a pharmaceutically acceptable salt or solvate thereof wherein each $R^3$ represents H or is selected from the group consisting of halo, CN, OH, $SCH_3$, $SO_2CH_3$, $C_{1-6}$alkyl, $C_{1-6}$alkoxy, halo$C_{1-6}$alkyl, halo$C_{1-6}$alkoxy and a 5-membered heteroaryl ring containing 1-2 nitrogen atoms and 0-1 oxygen atom, said ring being optionally substituted with 1-2 $C_{1-4}$alkyl groups.

More particularly, another aspect of the invention that is of interest relates to compounds in accordance with formula I or a pharmaceutically acceptable salt or solvate thereof wherein each $R^3$ represents H or is selected from the group consisting of halo which is selected from F, Cl and Br, CN, OH, $SCH_3$, $SO_2CH_3$, $C_{1-2}$alkyl, $C_{1-2}$alkoxy, halo$C_{1-2}$alkyl and halo$C_{1-2}$alkoxy wherein the halo portion of halo$C_{1-2}$alkyl and halo$C_{1-2}$alkoxy is selected from F and Cl, and a 5-membered heteroaryl ring containing 1-2 nitrogen atoms and 0-1 oxygen atom, said ring being optionally substituted with 1-2 $C_{1-4}$alkyl groups.

Even more particularly, another aspect of the invention that is of interest relates to compounds in accordance with formula I or a pharmaceutically acceptable salt or solvate thereof wherein each $R^3$ represents H, F, Cl, Br, CN, OH, $CH_3$, $OCH_3$, $OCH_2CH_3$, $CHF_2$, $CF_3$, $SCH_3$, $SO_2CH_3$, $OCHF_2$, $OCF_3$ and a 5-membered heteroaryl ring containing 1-2 nitrogen atoms, 0-1 oxygen atom and being optionally substituted with 1 $C_{1-2}$alkyl group.

Another aspect of the invention that is of interest relates to compounds in accordance with formula I or a pharmaceutically acceptable salt or solvate thereof wherein each $R^4$ represents H, halo selected from F and Cl, OH, $C_{1-2}$alkyl, $C_{1-2}$alkoxy, halo$C_{1-2}$alkyl and halo$C_{1-2}$alkoxy wherein the halo portion of halo$C_{1-2}$alkyl and halo$C_{1-2}$alkoxy is selected from F and Cl.

In particular, another aspect of the invention that is of interest relates to compounds in accordance with formula I or a pharmaceutically acceptable salt or solvate thereof wherein each $R^4$ represents H, F, Cl, OH, $CH_3$, $OCH_3$, $CF_3$, and $OCF_3$ More particularly, another aspect of the invention that is of interest relates to compounds in accordance with formula I or a pharmaceutically acceptable salt or solvate thereof wherein each $R^4$ represents H, F, $CH_3$ or OH.

Another aspect of the invention that is of interest relates to compounds in accordance with formula I or a pharmaceutically acceptable salt or solvate thereof wherein m represents 0 or 1 and Z represents tetrazolyl.

Another aspect of the invention that is of interest relates to compounds in accordance with formula I or a pharmaceutically acceptable salt or solvate thereof wherein m is 2 and Z represents $CO_2H$.

Another aspect of the invention that is of interest relates to compound in accordance with formula I or a pharmaceutically acceptable salt or solvate thereof wherein:
each $R^1$ represents H or is selected from the group consisting of halo, CN, $C_{1-6}$alkyl, $C_{1-6}$alkoxy, halo$C_{1-6}$alkyl and halo$C_{1-6}$alkoxy;
$R^2$ represents a member selected from the group consisting of: $C_{1-6}$alkyl and $C_{3-4}$alkenyl, each optionally substituted with 1-3 halo atoms;
each $R^3$ represents H or is selected from the group consisting of halo, CN, OH, $SCH_3$, $SO_2CH_3$, $C_{1-6}$alkyl, $C_{1-6}$alkoxy, halo$C_{1-6}$alkyl, halo$C_{1-6}$alkoxy and a 5-membered heteroaryl ring containing 1-2 nitrogen atoms and 0-1 oxygen atom, said ring being optionally substituted with 1-2 $C_{1-4}$alkyl groups;
each $R^4$ represents H, halo selected from F and Cl, OH, $C_{1-2}$alkyl, $C_{1-2}$alkoxy, halo$C_{1-2}$alkyl and halo$C_{1-2}$alkoxy wherein the halo portion of halo$C_{1-2}$alkyl and halo$C_{1-2}$alkoxy is selected from F and Cl;
m is 0 or 1 and Z is tetrazolyl, or m is 2 and Z represents $CO_2H$.

Examples of compounds that fall within the invention described herein are in the tables and examples contained herein. Pharmaceutically acceptable salts and solvates of the compounds disclosed in the tables are included as well.

Another aspect of the invention that is of interest relates to a pharmaceutical composition comprising a compound as described above with respect to formula I or a pharmaceutically acceptable salt or solvate thereof in combination with a pharmaceutically acceptable carrier.

Another aspect of the invention that is of interest relates to a method of treating type 2 diabetes mellitus in a mammalian patient in need of such treatment comprising administering to said patient a compound as described above with respect to formula I or a pharmaceutically acceptable salt or solvate thereof in an amount that is effective to treat type 2 diabetes mellitus.

Another aspect of the invention that is of interest relates to a method of delaying the onset of type 2 diabetes mellitus in a mammalian patient in need thereof, comprising administering to the patient a compound as described above in accordance with formula I or a pharmaceutically acceptable salt or solvate thereof in an amount that is effective to delay the onset of type 2 diabetes mellitus.

Another aspect of the invention that is of interest relates to a method of treating hyperglycemia, diabetes or insulin resistance in a mammalian patient in need of such treatment which comprises administering to said patient a compound as described above in accordance with formula I or a pharmaceutically acceptable salt or solvate thereof in an amount that is effective to treat hyperglycemia, diabetes or insulin resistance.

Another aspect of the invention that is of interest relates to a method of treating non-insulin dependent diabetes mellitus in a mammalian patient in need of such treatment comprising administering to the patient an anti-diabetic effective amount of a compound in accordance with formula I or a pharmaceutically acceptable salt or solvate thereof as described above.

Another aspect of the invention that is of interest relates to a method of treating obesity in a mammalian patient in need of such treatment comprising administering to said patient a compound in accordance with formula I as described above or a pharmaceutically acceptable salt or solvate thereof in an amount that is effective to treat obesity.

Another aspect of the invention that is of interest relates to a method of treating Syndrome X in a mammalian patient in need of such treatment, comprising administering to said patient a compound in accordance with formula I as described above or a pharmaceutically acceptable salt or solvate thereof in an amount that is effective to treat Syndrome X.

Another aspect of the invention that is of interest relates to a method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound as described above with respect to formula I or a pharmaceutically acceptable salt or solvate thereof in an amount that is effective to treat said lipid disorder.

Another aspect of the invention that is of interest relates to a method of treating atherosclerosis in a mammalian patient in need of such treatment, comprising administering to said patient a compound in accordance with formula I as described above or a pharmaceutically acceptable salt or solvate thereof in an amount effective to treat atherosclerosis.

Another aspect of the invention that is of interest relates to a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I as described above or a pharmaceutically acceptable salt or solvate thereof in an amount that is effective to treat said condition.

Another aspect of the invention that is of interest relates to a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound in accordance with formula I as described above or a pharmaceutically acceptable salt or solvate thereof in an amount that is effective to delay the onset of said condition.

Another aspect of the invention that is of interest relates to a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I as described above or a pharmaceutically acceptable salt or solvate thereof in an amount that is effective to reduce the risk of developing said condition.

Another aspect of the invention that is of interest relates to a method of treating a condition selected from the group consisting of:

(1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (1.3) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient effective amounts of a compound of formula I as described above, or a pharmaceutically acceptable salt or solvate thereof, and a another compound that is selected from the list provided below.

(1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; and EPO Application No. EP-658546, EP-656354, EP-576357; (4) anti-obesity serotonergic agents, such as fenfluramine, dexfenfluramine, phentermine, and sibutramine; (5)β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. Pat. No. 5,705,515, and U.S. Pat. No. 5,451,677 and PCT Patent Publications WO94/18161, WO95/29159, WO97/46556, WO98/04526 and WO98/32753, WO 01/74782, and WO 02/32897; (6) pancreatic lipase inhibitors, such as orlistat (Xenical®), cetilistat, Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, hereby incorporated by reference in their entirety; European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027, and Japanese Patent Application Nos. JP 13226269, and JP 2004-139909; (11) melanin-concentrating hormone 2 receptor (MCH2R) agonist/antagonists; (12) orexin-1 receptor antagonists, such as SB-334867-A, and those disclosed in PCT Patent Application Nos. WO 01/96302, WO 01/68609, WO 02/51232, and WO 02/51838; (13) serotonin reuptake inhibitors such as fluoxetine, paroxetine, and sertraline, and those disclosed in U.S. Pat. No. 6,365,633, and PCT Patent Application Nos. WO 01/27060 and WO 01/162341; (14) melanocortin agonists, such as Melanotan II, CHIR86036 (Chiron), ME-10142, and ME-10145 (Melacure), CHIR86036 (Chiron); PT-141, and PT-14 (Palatin); (15) other MC4R (melanocortin 4 receptor) agonists, such as those disclosed in: U.S. Pat. Nos. 6,410,548; 6,294, 534; 6,350,760; 6,458,790; 6,472,398; 6,376,509; and 6,818, 658; US Patent Publication No. US2002/0137664; US2003/ 0236262; US2004/009751; US2004/0092501; and PCT Application Nos. WO 99/64002; WO 00/74679; WO 01/70708; WO 01/70337; WO 01/74844; WO 01/91752; WO 01/991752; WO 02/15909; WO 02/059095; WO 02/059107; WO 02/059108; WO 02/059117; WO 02/067869; WO 02/068387; WO 02/068388; WO 02/067869; WO 02/11715; WO 02/12166; WO 02/12178; WO 03/007949; WO 03/009847; WO 04/024720; WO 04/078716; WO 04/078717; WO 04/087159; WO 04/089307; and WO 05/009950; (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-1 agonists (cholecystokinin-A) agonists, such as AR-R 15849, GI 181771, JMV-180, A-71378, A-71623 and SR146131, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and those described and disclosed in PCT Application No. WO 02/15905, and O—[3-(1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (25) β-hydroxy steroid dehydrogenase-1 inhibitors (β-HSD-1); (26) PDE (phosphodiesterase) inhibitors, such as theophylline, pentoxifylline, zaprinast, sildenafil, aminone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives, such as those disclosed in U.S. Pat. Nos. 5,552, 524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (32) other BRS3 (bombesin receptor subtype 3) agonists such as [D-Phe6,beta-Ala11, Phe13,Nle14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron), and those disclosed in PCT Application Nos. WO 94/09134, WO 98/22128, and WO 99/43813; (35) monoamine reuptake inhibitors, such as sibutramine, and those disclosed in U.S. Pat. Nos. 4,746,680, 4,806,570, and 5,436,272, U.S. Patent Publication No. 2002/0006964 and PCT Application Nos. WO 01/27068, and WO 01/62341; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (37) thyroid hormone β agonists, such as KB-2611 (KaroBioBMS), and those disclosed in PCT Application No. WO 02/15845, and Japanese Patent Application No. JP 2000256190; (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444 and sitagliptin; and the compounds disclosed in U.S. Pat. No. 6,699,871, which is incorporated herein by reference; and International Patent Application Nos. WO 03/004498; WO 03/004496; EP 1 258 476; WO 02/083128; WO 03/000250; WO 03/002530; WO 03/002531; WO 03/002553; WO 03/002593; WO 03/000180; and WO 03/000181; (45) dicarboxylate transporter inhibitors; (46) glucose transporter inhibitors; (47) phosphate transporter inhibitors; (48) Metformin (Glucophage®); (49) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)), and those disclosed in U.S. Pat. No. 5,026,685, U.S. Pat. No. 5,604,203, U.S. Pat. No. 5,574,010, U.S. Pat. No. 5,696,093, U.S. Pat. No. 5,936, 092, U.S. Pat. No. 6,046,162, U.S. Pat. No. 6,046,167, U.S. Pat. No. 6,093,692, U.S. Pat. No. 6,225,445, U.S. Pat. No. 5,604,203, U.S. Pat. No. 4,002,531, U.S. Pat. No. 4,179,337, U.S. Pat. No. 5,122,614, U.S. Pat. No. 5,349,052, U.S. Pat. No. 5,552,520, U.S. Pat. No. 6,127,355, WO 95/06058, WO 98/32466, WO 03/026591, WO 03/057235, WO 03/027637, and WO 2004/066966; (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (53) cyclooxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (54) Neuropeptide Y1 (NPY1) antagonists such as BIBP3226, J-115814, BIBO 3304, LY-357897, CP-671906, GI-264879A and those disclosed in U.S. Pat. No. 6,001,836; and PCT Application Nos. WO 96/14307, WO 01/23387, WO 99/51600, WO 01/85690, WO 01/85098, WO 01/85173, and WO 01/89528; (55) Opioid antagonists such as nalmefene (Revex®), 3-methoxynaltrexone, naloxone, naltrexone, and those disclosed in: PCT Application No. WO 00/21509; (57) 11β HSD-1 (11-beta hydroxy steroid dehydrogenase type 1) inhibitors such as BVT 3498, BVT 2733, and those disclosed in WO 01/90091, WO 01/90090, WO 01/90092, and U.S. Pat. No. 6,730,690 and US Publication No. US 2004-0133011, which are incorporated by reference herein in their entirety; (56) aminorex; (57) amphechloral; (58) amphetamine; (59) benzphetamine; (60) chlorphentermine; (61) clobenzorex; (62) cloforex; (63) clominorex; (64) clortermine; (65) cyclexedrine; (66) dextroamphetamine; (67) diphemethoxidine, (68) N-ethylamphetamine; (69) fenbutrazate; (70) fenisorex; (71) fenproporex; (72) fludorex; (73) fluminorex; (74) furfurylmethylamphetamine; (75) levamfetamine; (76) levophacetoperane; (77) mefenorex; (78) metamfepramone; (79) methamphetamine; (80) norpseudoephedrine; (81) pentorex; (82) phendimetrazine; (83) phenmetrazine; (84) picilorex; (85) phytopharm 57; (86) zonisamide, (87) neuromedin U and analogs or derivatives thereof, (88) oxyntomodulin and analogs or derivatives thereof, (89) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699; (90) Qnexa; (91) smoking cessation agents, such as nicotine agonists, partial nicotine agonists, such as varenicline, monoamine oxidase inhibitors (MAOIs), antidepressants such as bupropion, doxepine, and nortriptyline; and anxiolytic agents such as buspirone or clonidine.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl) {3-[(1S)-1-(3,5-difluorophenyl)-2-hydroxy-2-methylpropyl]azetidin-1-yl}methyl)benzonitrile, 3-((S)-(4-chlorophenyl) {3-[(1S)-1-(3,5-difluorophenyl)-2-fluoro-2-methylpropyl]azetidin-1-yl}methyl)benzonitrile, 3-((4-chlorophenyl) {3-[1-(3,5-difluorophenyl)-2,2-dimethylpropyl]azetidin-1-yl}methyl) benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl) (3-{(1S)-2-fluoro-1-[3-fluoro-5-(4H-1,2,4-triazol-4-yl) phenyl]-2-methylpropyl}azetidin-1-yl)methyl]benzonitrile, and 5-((4-chlorophenyl) {3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl) methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl] benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl) (3-{(1S)-2-fluoro-1-[3-fluoro-5-(1,3,4-oxadiazol-2-yl) phenyl]-2-methylpropyl}azetidin-1-yl)methyl]benzonitrile, 3-[(S)-(4-chlorophenyl)(3-{(1S)-2-fluoro-1-[3-fluoro-5-(1, 2,4-oxadiazol-3-yl)phenyl]-2-methylpropyl}azetidin-1-yl) methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl) azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl] benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl] benzonitrile, 5-{3-[(S)-{3-[(1S)-1-(3-bromo-5-fluorophenyl)-2-fluoro-2-methylpropyl]azetidin-1-yl}(4- chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl) [3-(1,3,4-oxadiazol-2-yl)phenyl]methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl] (4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl]methyl}azetidin-3-yl)-2-fluoro-2-methylpropyl]-5-fluorobenzonitrile, 3-[(1S)-1-(1-{(S)-(4-chlorophenyl) [3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2 (311)-one, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl]azetidin-1-yl}[3-(5-oxo-4,5-dihydro-1,3,4-oxadiazol-2-yl)phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H), 4'-piperidine]-1'-carboxamide, 3-oxo-N-(7-trifluoromethylpyrido[3,2-b]pyridin-2-yl)spiro-[isobenzofuran-1(3H), 4'-piperidine]-1'-carboxamide, N-[5-(3-fluorophenyl)-2-pyrimidinyl]-3-oxospiro-[isobenzofuran-1(3H), 4'-piperidine]-1'-carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1 (3H), 1'-cyclohexane]-4'-carboxamide, trans-N-[5-(3-fluorophenyl)-2-pyrimidinyl]-3-oxospiro[5-azaisobenzofuran-1(3H), 1'-cyclohexane]-4'-carboxamide, trans-N-[5-(2-fluorophenyl)-2-pyrimidinyl]-3-oxospiro[5-azaisobenzofuran-1(3H), 1'-cyclohexane]-4'-carboxamide, trans-N-[1-(3,5-difluorophenyl)-4-imidazolyl]-3-oxospiro [7-azaisobenzofuran-1(3H), 1'-cyclohexane]-4'-carboxamide, trans-3-oxo-N-(1-phenyl-4-pyrazolyl)spiro[4-azaisobenzofuran-1(3H), 1'-cyclohexane]-4'-carboxamide, trans-N-[1-(2-fluorophenyl)-3-pyrazolyl]-3-oxospiro[6-azaisobenzofuran-1(3H), 1'-cyclohexane]-4'-carboxamide, trans-3-oxo-N-(1-phenyl-3-pyrazolyl)spiro[6-azaisobenzofuran-1(3H), 1'-cyclohexane]-4'-carboxamide, trans-3-oxo-N-(2-phenyl-1,2,3-triazol-4-yl)spiro[6-azaisobenzofuran-1 (3H), 1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl) spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro [chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro [chroman-2,4'-piperidin]-4-one; and pharmaceutically acceptable salts and esters thereof. Specific MCH1R antagonist compounds of use in combination with a compound of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4[(1-isopropylazetidin-3-yl)oxy] phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl) oxy]phenyl}pyridin-2(1H)-one, 4-[(5-chloropyridin-2-yl) methoxy]-1-{4-[(1-propylazetidin-3-yl)oxy] phenyl}pyridin-2(1H)-one, and 4-[(5-chloropyridin-2-yl) methoxy]-1-(4-{[(2S)-1-ethylazetidin-2-yl] methoxy}phenyl)pyridin-2(1H)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a] pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl] propoxy}phenyl)pyrido[2,3-d]pyrimidin-4(3H)-one 2-methyl-3-(4-{3-[(3S)-3-methylpiperidin-1-yl] propoxy}phenyl)pyrido[4,3-d]pyrimidin-4(3H)-one, 3-{4-[(1-cyclobutyl-4-piperidinyl)oxy]phenyl}-2,5-dimethyl-4 (3H)-quinazolinone, 3-{4-[(1-cyclobutyl-4-piperidinyl)oxy] phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4 (3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy] phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy] phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl) propoxy]phenyl}-4(3H)-quinazolinone, 5-methoxy-2-methyl-3-(4-{3-[(3S)-3-methylpiperidin-1-yl] propoxy}phenyl)-4(3H)-quinazolinone, 7-methoxy-2-methyl-3-(4-{3-[(3S)-3-methylpiperidin-1-yl] propoxy}phenyl)-4(3H)-quinazolinone, 2-methyl-3-(4-{3-

[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl] propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl] carbonyl}-1-piperazinyl)-1-naphthoic acid; 3-(4-{[1-(3-ethoxyphenyl)-2-(4-fluorophenyl)-1H-imidazol-4-yl] carbonyl}-1-piperazinyl)-1-naphthoic acid; 3-(4-{[1-(3-ethoxyphenyl)-2-(2,4-difluorophenyl)-1H-imidazol-4-yl] carbonyl}-1-piperazinyl)-1-naphthoic acid; and 3-(4-{[1-(2, 3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-(1-(1-methyl-1H-1,2,4-triazol-5-yl) ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-{3-chloro-2-methyl-5-[1-methyl-1-(1-methyl-1H-1,2,4-triazol-5-yl)ethyl]-1'H, 5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({ (1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof. Still further, neurokinin-1 (NK-1) receptor antagonists may be favorably employed in combination with a compound of the present invention. NK-1 receptor antagonists of use in the present invention are fully described in the art. Specific neurokinin-1 receptor antagonists of use in the present invention include: (±)-(2R3R,2S3S)—N-{[2-cyclopropoxy-5-(trifluoromethoxy)-phenyl]methyl}-2-phenylpiperidin-3-amine; 2-(R)-(1-(R)-(3,5-bis(trifluoromethyl)phenyl)ethoxy)-3-(S)-(4-fluorophenyl)-4-(3-(5-oxo-1H,4H-1,2, 4-triazolo)methyl)morpholine; aperpitant; CJ17493; GW597599; GW679769; R673; R067319; R1124; R1204; SSR146977; SSR240600; T-2328; and T2763; or a pharmaceutically acceptable salts thereof. Examples of other anti-obesity agents that can be employed in combination with a compound of formula I are disclosed in "Patent focus on new anti-obesity agents," *Exp. Opin. Ther. Patents,* 10: 819-831 (2000); "Novel anti-obesity drugs," *Exp. Opin. Invest. Drugs,* 9: 1317-1326 (2000); and "Recent advances in feeding suppressing agents: potential therapeutic strategy for the treatment of obesity, *Exp. Opin. Ther. Patents,* 11: 1677-1692 (2001). The role of neuropeptide Y in obesity is discussed in *Exp. Opin. Invest. Drugs,* 9: 1327-1346 (2000). Cannabinoid receptor ligands are discussed in *Exp. Opin. Invest. Drugs,* 9: 1553-1571 (2000).

Another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor.

More particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor wherein the HMG-CoA reductase inhibitor is a statin.

Even more particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor, wherein the HMG CoA reductase inhibitor is a statin selected from the group consisting of lovastatin, simvastatin, pravastatin, fluvastatin, atorvastatin, itavastatin, rosuvastatin and rivastatin.

Another aspect of the invention that is of interest relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions, delaying the onset or reducing the risk of developing said condition, comprising administering to a mammalian patient in need of such treatment therapeutically effective amounts of a compound of formula I as described above and an HMG-CoA reductase inhibitor.

More particularly, another aspect of the invention that is of interest relates to a method for delaying the onset of, or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin, and even more particularly, a statin selected from the group consisting of: lovastatin, simvastatin, pravastatin, fluvastatin, atorvastatin, itavastatin, rosuvastatin and rivastatin.

Yet even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is simvastatin, atorvastatin or rosuvastatin.

Another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor. More particularly, another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor wherein the cholesterol absorption inhibitor is ezetimibe.

Another aspect of the invention that is of interest relates to a method for delaying the onset or reducing the risk of developing the other diseases and conditions mentioned above, in a mammalian patient in need of such treatment comprising administering to said patient effective amounts of a compound of formula I as described above, and a cholesterol absorption inhibitor.

More particularly, another aspect of the invention that is of interest relates to a method for delaying the onset or reducing the risk of developing the other diseases and conditions mentioned above, in a human patient in need of such treatment comprising administering to said patient effective amounts of a compound of formula I as described above, and a cholesterol absorption inhibitor, wherein the cholesterol absorption inhibitor is ezetimibe.

Another aspect of the invention that is of interest relates to a method of treating, delaying the onset, or preventing a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I or a pharmaceutically acceptable salt or solvate thereof, and a CETP inhibiting compound.

More particularly, an aspect of the invention that is of interest relates to a method of treating, delaying the onset, or preventing a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I or a pharmaceutically acceptable salt or solvate thereof, and a CETP inhibiting compound selected from torcetrapib and anacetrapib.

Another aspect of the invention that is of interest relates to a pharmaceutical composition comprising (1) a compound of formula I as described above; (2) a compound selected from the list provide above in combination with a pharmaceutically acceptable carrier.

One pharmaceutical composition that is of interest is comprised of a compound of formula I as described herein, or a pharmaceutically acceptable salt or solvate thereof, in combination with a DPP-IV inhibitor selected from the group consisting of:

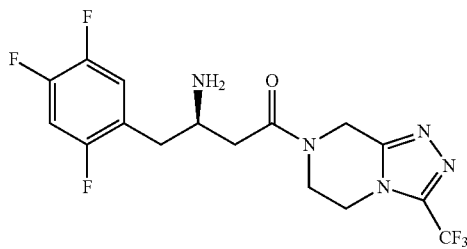

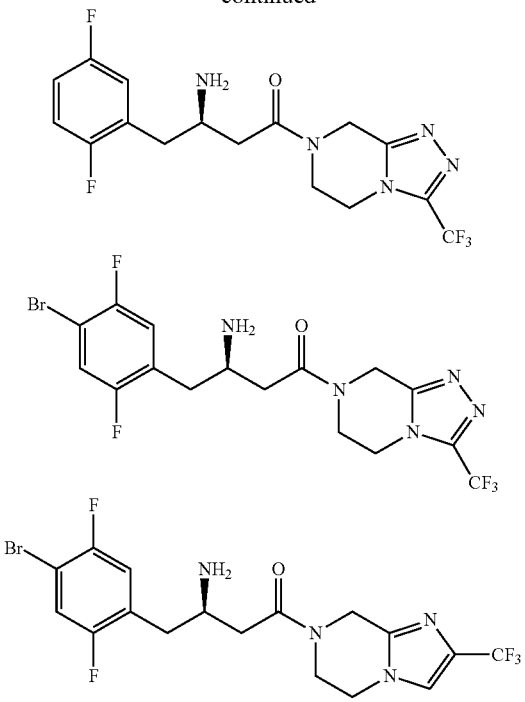

or a pharmaceutically acceptable salt or solvate thereof in combination with a pharmaceutically acceptable carrier.

Optical Isomers—Diastereomers—Geometric Isomers—Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixtures thereof are encompassed with the compounds of Formula I.

Salts and Solvates

Salts and solvates of compounds of formula I are included in the present invention. The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I are intended to include the pharmaceutically acceptable salts and solvates.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within the formulas described herein can be prepared without undue experimentation by conventional techniques well known to those skilled in the art or by processes analogous to those described in the Schemes and Examples herein using appropriate isotopically-enriched reagents and/or intermediates.

This invention relates to a method of inhibiting the activity of glucagon by antagonizing the glucagon receptor, thereby reducing the rate of gluconeogenesis and glycogenolysis, and the concentration of glucose in plasma.

The compounds of formula I can be used in the manufacture of a medicament for the prophylactic or therapeutic treatment of disease states in mammals associated with elevated levels of glucose, comprised of combining the compound of formula I with the carrier materials to provide the medicament.

Dose Ranges

The prophylactic or therapeutic dose of a compound of formula I will, of course, vary with the nature or severity of the condition to be treated, the particular compound selected and its route of administration. It will also vary according to the age, weight and response of the individual patient. In general, the daily dose range lies within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount", "anti-diabetic effective amount" and the other terms appearing throughout the application addressing the amount of the compound to be used refer to the dosage ranges provided, taking into account any necessary variation outside of these ranges, as determined by the skilled physician.

Representative dosages of compounds of formula I, as well as the pharmaceutically acceptable salts and solvates thereof, for adults range from about 0.1 mg to about 1.0 g per day, preferably about 1 mg to about 500 mg, in single or divided doses. Examples of suitable dosages include 0.1 mg, 1 mg, 2 mg, 5 mg, 10 mg, 20 mg, 40 mg, 50 mg, 75 mg, 100 mg, 150 mg, 200 mg, 250 mg, 500 mg, 1000 mg and similar such doses. Representative dosages of compounds used in combination with the compounds of formula I are known, or the determination thereof is within the level of skill in the art, taking into account the description provided herein.

When intravenous or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of formula I per kg of body weight per day.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human, with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like, in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets. Solid oral preparations are preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-inoil liquid emulsion. Such compositions may be prepared by any acceptable pharmaceutical process. All such methods include the step of combining the active ingredient(s) with the carrier components. In general, the compositions are prepared by uniformly and intimately admixing the active ingredient(s) with a liquid or finely divided solid carrier component, and then, if necessary, manipulating the blend into the desired product form. For example, a tablet may be prepared by compression or molding. Compressed tablets may be prepared by compressing free-flowing powder or granules, containing the active(s) optionally mixed with one or more excipients, e.g., binders, lubricants, diluents, surfactants and dispersants. Molded tablets may be made by molding a mixture of the powdered compound moistened with an inert liquid. Desirably, each tablet may contain, for example, from about 0.1 mg to about 1.0 g of the active ingredient and each cachet or capsule contains from about 0.1 mg to about 500 mg of the active ingredient.

The following are examples of pharmaceutical dosage forms containing a compound of Formula I:

gliptin, vildagliptin, saxagliptin, and the like, such as those disclosed in U.S. Pat. No. 6,699,871B1 granted on Mar. 2, 2004 (g) LXR modulators and (h) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide), and CB1 inhibitors, such as rimonabant and those compounds disclosed in WO03/077847A2 published on Sep. 25, 2003 and in WO05/000809 A1 published on Jan. 6, 2005.

An aspect of the invention that is particular interest relates to a pharmaceutical composition that is comprised of a compound of formula I, or a pharmaceutically acceptable salt thereof, and a member selected from the group consisting of: simvastatin, mevastatin, ezetimibe, atorvastatin, metformin, sibutramine, orlistat, Qnexa, topiramate, naltrexone, bupriopion, phentermine, losartan, hydrochlorothiazide, buformin, phenformin, troglitazone, pioglitazone, rosiglitazone, insulin, somatostatin, voglibose, miglitol, acarbose, sitagliptin, vildagliptin, saxagliptin, alogliptin, acetohexamide, carbuta-

| INJECTABLE SUSPENSION (IM.) | MG/ML | TABLET | MG/TABLET |
|---|---|---|---|
| COMPOUND OF FORMULA 1 | 10.0 | COMPOUND OF FORMULA 1 | 25.0 |
| METHYLCELLULOSE | 5.0 | MICROCRYSTALLINE CELLULOSE | 415 |
| TWEEN 80 | 0.5 | POVIDONE | 14.0 |
| BENZYL ALCOHOL | 9.0 | PREGELATINIZED STARCH | 4.0 |
| BENZALKONIUM CHLORIDE | 1.0 | MAGNESIUM STEARATE | 2.5 |
| WATER FOR INJECTION | T.D. 1.0 ML | TOTAL (APPROX.) | 460 MG |

| CAPSULE | MG/CAPSULE | AEROSOL | PER CANISTER |
|---|---|---|---|
| COMPOUND OF FORMULA 1 | 25.0 | COMPOUND OF FORMULA 1 | 250 MG |
| LACTOSE | 735 | LECITHIN, NF LIQ. CONC. | 1.2 MG |
| MG STEARATE | 1.5 | TRICHLOROMETHANE, NF | 4.025 G |
| TOTAL (APPROX.) | 761.5 MG | DICHLORODIFLUOROMETHANE, NF | 12.15 G |

Combination Therapy

As previously described, the compounds of Formula I may be used in combination with other drugs that are used in the treatment/prevention/delaying the onset of type 2 diabetes mellitus, as well as other diseases and conditions described herein, for which compounds of Formula I are useful. Other drugs may be administered, by a route and in an amount commonly used, contemporaneously or sequentially with a compound of Formula I. When a compound of Formula I is used contemporaneously with one or more other drugs, a combination pharmaceutical composition containing such other drugs in addition to the compound of Formula I is preferred. Accordingly, the pharmaceutical compositions of the present invention include those that alternatively contain one or more other active ingredients, in addition to a compound of Formula I. Examples of other active ingredients that may be combined with a compound of Formula I, either administered separately or in the same pharmaceutical compositions, include, but are not limited to: (a) biguanides (e.g., buformin, metformin, phenformin), (b) PPAR agonists (e.g., troglitazone, pioglitazone, rosiglitazone), (c) insulin, (d) somatostatin, (e) alpha-glucosidase inhibitors (e.g., voglibose, miglitol, acarbose), (f) DPP-IV inhibitors, such as sitamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide, rimonabant and taranabant, in combination with a pharmaceutically acceptable carrier.

The weight ratio of the compound of the Formula I to the second active ingredient may be varied within wide limits and depends upon the effective dose of each active ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

When used in combination with other agents, the dosages noted above for the glucagon antagonist are provided along with the usual dose for the other medication. For example, when a DPP-IV inhibitor such as those disclosed in U.S. Pat. No. 6,699,871B1, is included, the DPP-IV inhibitor can be used in an amount ranging from about 1.0 mg to as high as about 1000 mg, preferably about 2.5 mg to about 250 mg, and in particular, about 50 mg or about 100 mg administered in single daily doses or in divided doses as appropriate. Similarly, when the glucagon receptor antagonist is used in combination with a CB1 antagonist/inverse agonist, the CB1 antagonist/inverse agonist can be used in an amount ranging from as low as about 0.1 mg to as high as about 1000 mg, more particularly, in an amout ranging from about 1.0 mg to about 100 mg, and even more particularly, in an amount from about 1.0 mg to about 10 mg, administered in single daily doses or in divided doses as appropriate. Examples of doses of CB1 antagonist/inverse agonist include 1 mg, 2 mg, 3 mg, 4 mg, 5 mg, 6 mg, 7 mg, 8 mg, 9 mg, 10 mg and 20 mg.

Methods of Synthesis:

Compounds of the present invention can be prepared according to the Schemes provided below as well as the procedures provided in the Examples. The substituents are the same as in the above Formulas except where defined otherwise or otherwise apparent to the ordinary skilled artisan.

The novel compounds of the present invention can be readily synthesized using techniques known to those skilled in the art, such as those described, for example, in *Advanced Organic Chemistry*, March, $5^{th}$ Ed., John Wiley and Sons, New York, N.Y., 2001; *Advanced Organic Chemistry*, Carey and Sundberg, Vol. A and B, $3^{rd}$ Ed., Plenum Press, Inc., New York, N.Y., 1990; *Protective groups in Organic Synthesis*, Green and Wuts, $2^{nd}$ Ed., John Wiley and Sons, New York, N.Y., 1991; *Comprehensive Organic Transformations*, Larock, VCH Publishers, Inc., New York, N.Y., 1988; *Handbook of Heterocyclic Chemistry*, Katritzky and Pozharskii, $2^{nd}$ Ed., Pergamon, New York, N.Y., 2000 and references cited therein. The starting materials for the present compounds may be prepared using standard synthetic transformations of chemical precursors that are readily available from commercial sources, including Aldrich Chemical Co. (Milwaukee, Wis.); Sigma Chemical Co. (St. Louis, Mo.); Lancaster Synthesis (Windham, N.H.); Ryan Scientific (Columbia, S.C.); Maybridge (Cornwall, UK); Matrix Scientific (Columbia, S.C.); Acros, (Pittsburgh, Pa.); BioBlocks, Inc. (San Diego, Calif.); and Trans World Chemicals (Rockville, Md.).

The procedures described herein for synthesizing the compounds may include one or more steps of protecting group manipulations and of purification, such as, re-crystallization, distillation, column chromatography, flash chromatography, thin-layer chromatography (TLC), and high-pressure chromatography (HPLC). The products can be characterized using various techniques well known in the chemical arts, including proton and carbon-13 nuclear magnetic resonance ($^1$H and $^{13}$C NMR), infrared and ultraviolet spectroscopy (IR and UV), X-ray crystallography, elemental analysis and HPLC and mass spectrometry (HPLC-MS). Methods of protecting group manipulation, purification, structure identification and quantification are well known to one skilled in the art of chemical synthesis.

Appropriate solvents are those which will at least partially dissolve one or all of the reactants and will not adversely interact with either the reactants or the product. Suitable solvents are aromatic hydrocarbons (e.g, toluene, xylenes), halogenated solvents (e.g, methylene chloride, chloroform, carbontetrachloride, chlorobenzenes), ethers (e.g, diethyl ether, diisopropylether, tert-butyl methyl ether, diglyme, tetrahydrofuran, dioxane, anisole), nitriles (e.g, acetonitrile, propionitrile), ketones (e.g, 2-butanone, dithyl ketone, tert-butyl methyl ketone), alcohols (e.g, methanol, ethanol, n-propanol, iso-propanol, n-butanol, t-butanol), N,N-dimethyl formamide (DMF), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, and calcium hydroxide; alkali metal hydrides and alkaline earth metal hydrides such as lithium hydride, sodium hydride, potassium hydride and calcium hydride; alkali metal amides such as lithium amide, sodium amide and potassium amide; alkali metal carbonates and alkaline earth metal carbonates such as lithium carbonate, sodium carbonate, cesium carbonate, sodium hydrogen carbonate, and cesium hydrogen carbonate; alkali metal alkoxides and alkaline earth metal alkoxides such as sodium methoxide, sodium ethoxide, potassium tert-butoxide and magnesium ethoxide; alkali metal alkyls such as methyllithium, n-butyllithium, sec-butyllithium, t-bultyl-lithium, phenyllithium, alkyl magnesium halides, organic bases such as trimethylamine, triethylamine, triisopropylamine, N,N-diisopropylethyl amine, piperidine, N-methyl piperidine, morpholine, N-methyl morpholine, pyridine, collidines, lutidines, and 4-dimethylaminopyridine; and bicyclic amines such as DBU and DABCO.

It is understood that the functional groups present in compounds described in the Schemes below can be further manipulated, when appropriate, using the standard functional group transformation techniques available to those skilled in the art, to provide desired compounds described in this invention.

Throughout the synthesis schemes, abbreviations are used with the following meanings unless otherwise indicated:

| | |
|---|---|
| AIBN = azobisisobutyronitrile | aq = aqueous |
| BINAP = 2,2'-bis(diphenylphosphino)-1,1'-binaphthalene | Bn = benzyl |
| BOC, Boc = t-butyloxycarbonyl | BOP = benzotriazol-1-yloxy-tris(dimethylamino)-phosphonium hexafluorophosphate |
| Bu = butyl, t-Bu = t-butyl | BuLi, n-BuLi = n-butyllithium |
| CBZ, Cbz = Benzyloxycarbonyl | CDI = 1,1'-carbonyldiimidazole |
| (S)-DAIPEN = (S)-1,1-di(4-anisyl)-2-isopropyl-1,2-ethylenediamine = (S)-1,1-bis(4-methoxyphenyl)-3-methylbutane-1,2-diamine | dba = dibenzylideneacetone = trans,trans-1,5-diphenyl-1,4-pentadien-3-one |
| DCM = dichloromethane | 2,4-diClPh = 2,4-dichlorophenyl |
| DIEA = diisopropylethylamine | DMAP = 4-Dimethylaminopyridine |
| DMF = N,N-dimethylformamide | DMS = dimethyl sulfide |
| DMSO = dimethyl sulfoxide | dppf = 1,1'-bis(diphenylphosphino)ferrocene |
| EDC = 1-ethyl-3-(3-dimethylaminopropyl)-carbodiimide | eq. = equivalent(s) |
| Et = ethyl | EtOAc = ethyl acetate |

| | |
|---|---|
| EtOH = ethanol | g = gram(s) |
| HOBT, HOBt = 1-hydroxybenzotriazole | HPLC = High pressure liquid chromatography |
| IPA = isopropanol = 2-propanol | iPr = isopropyl = 2-propyl |
| KHMDS = potassium bis(trimethylsilyl)amide | KOtBu = potassium tert-butoxide |
| LC/MS = liquid chromatography - mass spectrometry | LDA = lithium diisopropylamide |
| LHMDS = lithium bis(trimethylsilyl)amide | M = molar |
| mCPBA = 3-chloroperoxybenzoic acid | Me = methyl |
| MeCN, CH$_3$CN = acetonitrile | MeOH = methanol |
| mg = milligram(s) | mL = milliliter(s) |
| mmol = millimole(s) | N = normal |
| NaOtBu = sodium tert-butoxide | NBS = N-bromosuccinimide |
| NCS = N-chlorosuccinimide | n-Pr = n-propyl |
| PCC = pyridinium chlorochromate | Pd/C = palladium on activated carbon |
| Ph = phenyl | PyBOP = Benzotriazol-1-yloxytripyrrolidinophosphonium hexafluorophosphate |
| RT, rt = room temperature | TBAF = tetrabutylammonium fluoride |
| Tf = triflate = trifluoromethanesulfonate | TFA = Trifluoroacetic acid |
| THF = tetrahydrofuran | TMS = trimethylsilyl |
| Tr = trityl = triphenylmethyl | (S)-xyl-SEGPHOS = (S)-5,5'-Bis[di(3,5-xylyl)phosphino]-4,4'-bi-1,3-benzodioxole |

Compounds of the present invention may be prepared according to the methodology outlined in the following general synthetic schemes.

Multiple embodiments of the present invention are summarized in Scheme 1 which depicts the preparation of compounds Ia, Ib, and Ic from the acid 1. It is noted that the benzothiophene can be substituted with R$^3$ at any available point of attachment. Moreover, the benzothiophene can be attached to the remainder of the molecule at position 2 or 3. The carboxylic acid intermediate 1 is coupled with substituted or unsubstituted beta alanine ester (either methyl, ethyl or t-butyl ester) using benzotriazol-1-yloxy-tris(dimethylamino)-phosphonium hexafluorophosphate (BOP) and a base, generally N,N-diisopropylethylamine (DIEA), in a solvent such as N,N-dimethylformamide (DMF) or acetonitrile at ambient temperature to yield compound 2. Alternatively, the conversion of 1 to 2 may be carried out with EDC, HOBt, and a base such as DIEA in similar solvents as those used with BOP and DIEA. Many additional peptide coupling conditions are known and may also be used. Saponification of ester 2 (methyl, ethyl) to give compound Ia is achieved with a base such as aqueous lithium hydroxide (LiOH) or aqueous sodium hydroxide in a polar solvent such as tetrahydrofuran, methanol, ethanol or a mixture of similar solvents. In addition, compound 2, containing a t-butyl ester, can be converted to compound Ia using acid such as acetic acid or trifluoroacetic acid (TFA). In additional embodiments of the invention, compounds Ib and Ic may be prepared directly from acid 1 by coupling with the appropriately substituted amine using the peptide coupling methods described for the preparation of amide 2.

Scheme 1

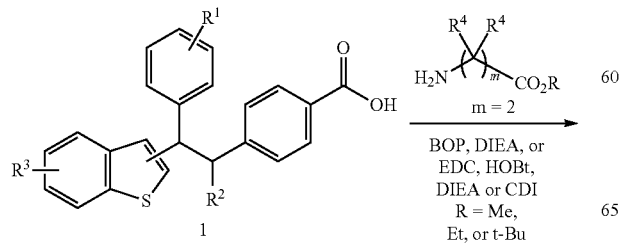

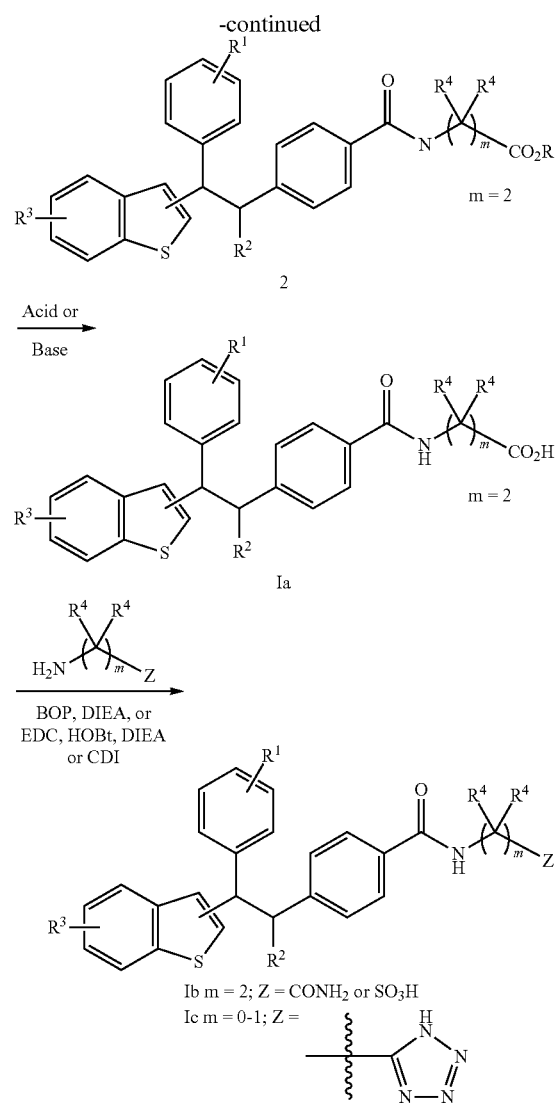

Scheme 2 summarizes the preparation of acid intermediate 1 using procedures adapted from *Organic Letters*, Chung, et. al., 2008, 10, 3037-3040. Coupling of aryl alkyl ketones 3 and aryl bromide 4 may be achieved under transition-metal mediated conditions such as those described in *J. Am. Chem. Soc.*, Buchwald, S. L., et. al., 2000, 122, 1360-1370. Ketone 5 may be prepared, for instance, by heating 3 and 4 in the presence of a palladium source such as $Pd_2(dba)_3$, a ligand such as BINAP, a base such as NaOtBu, and a solvent such as THF. Reduction of ketone 5 to alcohol 6 can be accomplished with various achiral reductants, for instance $NaBH_4$. Alternatively, dynamic kinetic resolution of ketone 5 can afford highly enantio- and diastereoenriched alcohol 6 using catalysts such as those reviewed extensively in *Angew. Chem., Int. Ed.*, Noyori, R., et. al., 2001, 40, 40-73. For instance, this reaction can be performed using a ruthenium catalyst such as $RuCl_2$-[(S)-xyl-SEGPHOS][(S)-DAIPEN] and a base such as KOtBu in a solvent such as 2-propanol under an atmosphere of hydrogen. Deprotection of the t-butyl ester of alcohol 6 with an acid such as phosphoric acid in acetonitrile solvent gives the acid 7.

Acid 1 may then be accessed by treatment of 7 with a benzothiophene 8 in dichloromethane solvent at ambient temperature or 60° C. followed by the addition of a Bronsted acid such as trifluoroacetic acid (TFA) or a Lewis acid such as boron trifluoride-diethyl etherate. A wide range of substituents may be introduced at $R^1$, $R^2$, and $R^3$ on acid 1 due to the functional group tolerance of the reactions employed in its preparation and the wide variety of starting benzothiophenes 8 and ketones 3 which are either commercially available or readily prepared by methods known to those skilled in the art.

Scheme 2

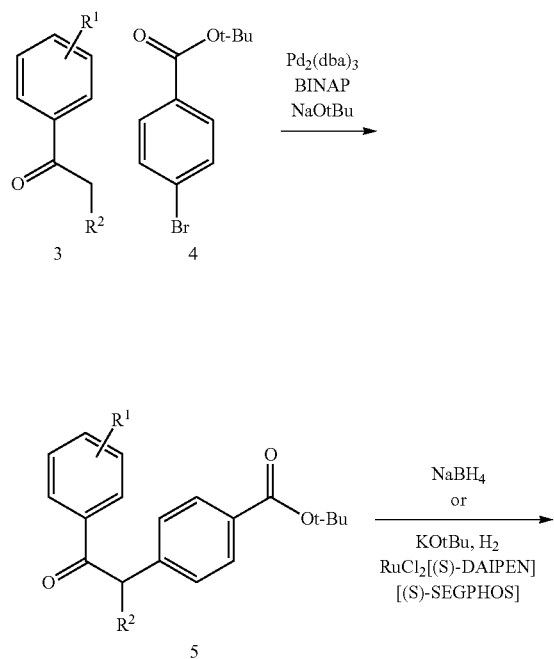

-continued

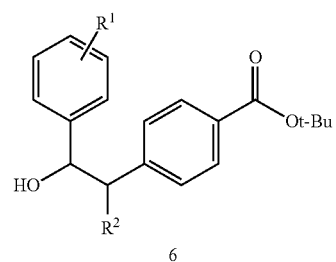

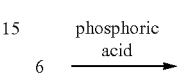

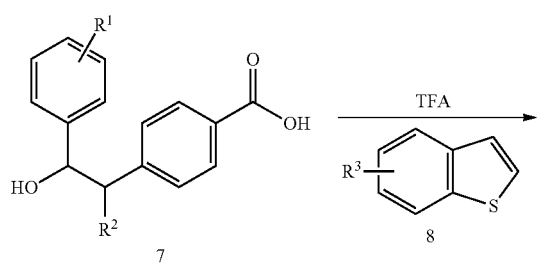

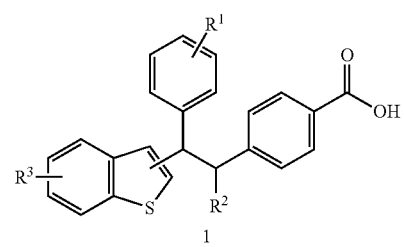

While the $R^3$ substituents are typically present in the starting material benzothiophene 8, it is also possible to alter the $R^3$ substituents on advanced intermediates as shown in Scheme 3. For instance, a bromide substituent may be further functionalized using a variety of metal-mediated cross-coupling reactions obvious to those skilled in the art. For instance, the bromide substituent of intermediate 2a may be converted to nitrile 2b in the presence of a palladium catalyst such as $Pd(PPh_3)_4$ and a cyanide source such as $Zn(CN)_2$ in a polar aprotic solvent such as DMF at a temperature of 80° C. based on the chemistry described by Kubota and Rice, *Tetrahedron Letters*, 1998, 39, 2907-2910. Alternatively, intermediate 2a can be functionalized under Suzuki coupling conditions with an aryl or heteroaryl boronic acid 9, palladium catalyst such as $PdCl_2(dppf)$, base such as LiOH, in a mixed solvent system such as dioxane and water, at elevated temperatures such as 80° C. Under these conditions, the ethyl ester of intermediate 2a can also be hydrolyzed to afford compound 1a directly. Numerous other metal-mediated functionalizations of intermediates such as 2a will be obvious to those skilled in the art.

Scheme 3

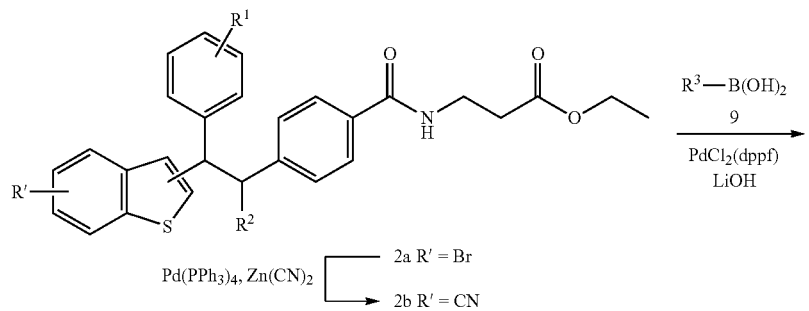

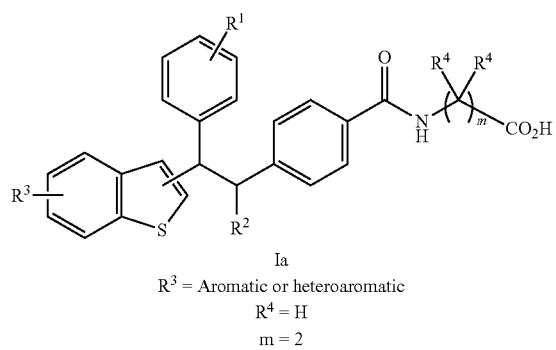

Ia
R³ = Aromatic or heteroaromatic
R⁴ = H
m = 2

While a variety of substituted benzothiophenes 8 are commercially available, two methods for synthesizing them are depicted in Scheme 4. When the appropriately substituted benzenethiol 10 is readily accessible, it may be alkylated with bromoacetaldehyde dimethyl acetal at elevated temperatures in the presence of a base such as potassium carbonate in a polar aprotic solvent such as DMF. The resulting acetal intermediate 11 can then undergo cyclocondensation to afford benzothiophene 8 upon heating in the presence of an acid such as polyphosphoric acid in a solvent such as chlorobenzene. An alternate preparation of benzothiophenes proceeds from aryl fluoride 12. Aryl fluorides such as 12 may be lithiated at the position adjacent to fluorine by a strong base such as lithium diisopropylamide in a solvent such as THF at low temperatures such as −70° C. The resulting intermediate can then react with a formyl electrophile such as DMF to afford the 2-fluorobenzaldehyde 13. Nucleophilic aromatic substitution of the fluorine substituent of 13 with methyl thioglycolate and subsequent cyclocondensation to benzothiophene 8a can be accomplished in a single vessel by heating the reactants in the presence of a base such as potassium carbonate in a solvent such as acetonitrile. If desired, the 2-carbomethoxy substituent of benzothiophene 8a may be removed to afford benzothiophene 8b. Saponification of the ester as described for the conversion of 2 to Ia (Scheme 1) yields an acid which may be decarboxylated using a variety of procedures known to those skilled in the art. For instance, the acid may be treated with copper powder in quinoline at a temperature of 200° C.

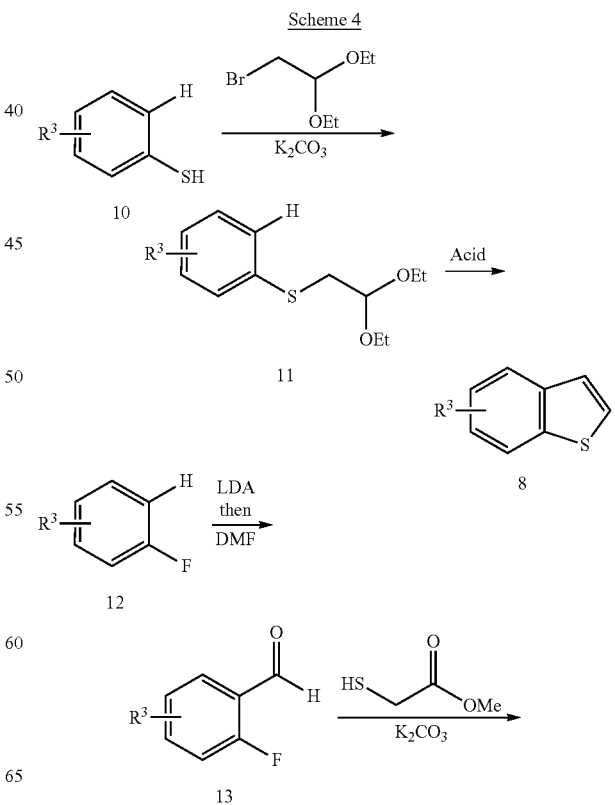

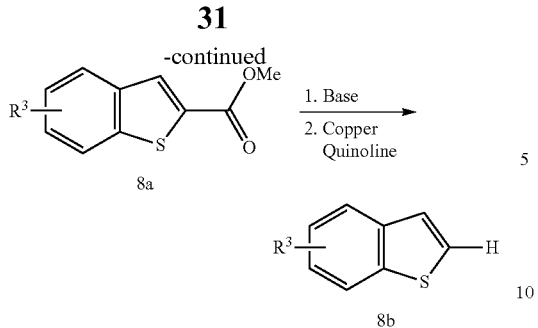

Separation of diastereomers and regioisomers can be carried out at various stages in the preparation of compounds I, however, it is typically carried out on compound I using reverse-phase HPLC or on the amide 2 using silica gel chromatography or preparative HPLC with a chiral stationary phase.

Analytical HPLC Mass Spectrometry Conditions:
LC1: Column: Waters Xterra MS C18 3.5μ, 3.0×50 mm
  Temperature: 50° C.
  Eluent: 10:90 to 100:0 v/v acetonitrile/water+0.05% formic acid over 3.75 min.
  Flow Rate: 1.2 mL/min, Injection 10 μL
  Detection: PDA, 200-600 nm
  MS: mass range 150-750 amu; positive/negative ion electrospray ionization
LC2: Column: Waters Xterra IS C-18, 3.5μ, 2.1×20 mm
  Temperature: 50° C.
  Eluent: 10:90 to 98:2 v/v acetonitrile/water+0.05% formic acid over 3.25 min.
  Flow Rate: 1.5 mL/min, Injection 5 μL
  Detection: PDA, 200-600 nm
  MS: mass range 150-750 amu; positive/negative ion electrospray ionization
LC3: Column. Waters Xterra IS C-18, 3.5μ, 2.1×20 mm
  Temperature: 50° C.
  Eluent: 10:90 to 98:2 v/v acetonitrile/water+0.05% TFA over 3.25 min.
  Flow Rate: 1.5 mL/min, Injection 5 μL
  Detection: PDA, 200-600 nm
  MS: mass range 150-750 amu; positive/negative ion electrospray ionization
LC4: Column. Waters Sunfire C18, 5μ, 4.6×50 mm
  Temperature: 50° C.
  Eluent: 10:90 to 100:0 v/v acetonitrile/water+0.05% TFA over 3.75 min.
  Flow Rate: 1.2 mL/min, Injection 10 μL
  Detection: PDA, 190-300 nm
  MS: mass range 150-700 amu; positive ion electrospray ionization
Preparative Reverse-Phase HPLC Conditions:
  Column: Kromasil 100-5-C18, 21.1×100 mm
  Flow Rate: 20.0 mL/min
  Eluent: 10:90 to 100:0 v/v acetonitrile/water+0.1% TFA over 10.0 min.
  Temperature: ambient
  Detection: PDA, 254 nm
  Preparative thin layer chromatography (PTLC) was performed on 20×20 cm plates (500 μm thick silica gel). Silica gel chromatography was done on a Biotage Horizon flash chromatography system.

The following examples are provided so that the invention might be more fully understood. They should not be construed as limiting the invention in any way.

Intermediate 1

4-{(1R)-1-[(R)-(4-CHLOROPHENYL)(HYDROXY)METHYL]BUTYL}BENZOIC ACID

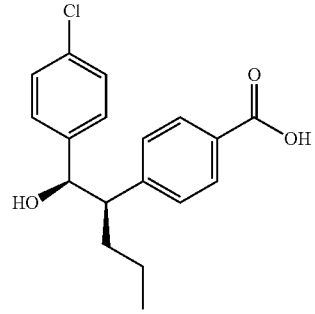 [SMILES: CCC[C@H](c1ccc(C(=O)O)cc1)[C@@H](O)c1ccc(Cl)cc1]

Step A. tert-Butyl 4-[2-(4-chlorophenyl)-1-propylethan-2-one-1-yl]benzoate

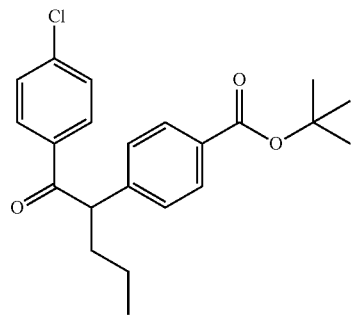 [SMILES: CCCC(C(=O)c1ccc(Cl)cc1)c1ccc(C(=O)OC(C)(C)C)cc1]

A 3-neck flask was charged with NaOtBu (2.85 g, 28.6 mmol) and dry THF (50 mL) under nitrogen. Tris(dibenzylideneacetone)dipalladium(0) (0.26 g, 0.28 mmol) and (S)-Tol-Binap (0.47 g, 0.69 mmol) were then added under nitrogen. After stirring for 15 min, 1-(4-chlorophenyl)pentan-1-one (4.21 g, 21.0 mmol) was added, followed by tert-butyl 4-bromobenzoate (5.0 g, 19.1 mmol) under nitrogen. The mixture was heated at 60° C. for 8 hours. The mixture was diluted with heptane (100 mL) and poured into a solution of saturated NaHCO$_3$ (aq) (60 mL) and ice (40 g). The resulting layers were separated, and the aqueous phase was back-extracted with methyl tert-butyl ether (50 mL). The combined organics were washed with saturated NaHCO$_3$ (aq) then 10% NaCl(aq). The organic solution was filtered through a bed of silica 60 (84 g, wetted with 1:1 methyl tert-butyl ether/heptane), and washed with 1:1 methyl tert-butyl ether/heptane (600 mL). The combined filtrate was concentrated to afford an orange oil that was used directly for the next step: $^1$H NMR (500 MHz, CDCl$_3$): δ 7.91 (d, J=8.1 Hz, 2H); 7.86 (d, J=8.4 Hz, 2H); 7.35 (d, J=8.4 Hz, 2H); 7.32 (d, J=8.2 Hz, 2H); 4.53

(t, J=7.2 Hz, 1H); 2.19-2.09 (m, 1H); 1.85-1.76 (m, 1H); 1.56 (s, 9H); 1.35-1.18 (m, 2H); 0.91 (t, J=7.3 Hz, 3H); LC1: 1.35 min. (M-tBu+H)$^+$ 317.

Step B. tert-Butyl 4-[(1R,2R)-2-(4-chlorophenyl)-1-propylethan-2-hydroxyl-1-yl]benzoate

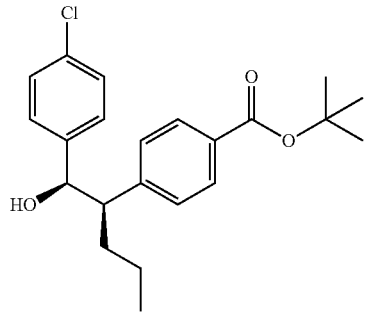 [SMILES: CCC[C@H](c1ccc(C(=O)OC(C)(C)C)cc1)[C@@H](O)c1ccc(Cl)cc1]

To degassed 2-propanol (5.0 mL) was added RuCl$_2$-[(S)-xyl-SEGPHOS][(S)-DAIPEN] (16.2 mg, 0.0134 mmol) and potassium t-butoxide (300 mg, 2.67 mmol). After this mixture was stirred at room temperature for 2 hours, the material obtained in Step A was added in 2-propanol (25 mL). This mixture was then treated with hydrogen (100 psi) at room temperature for 18 hours. The mixture was concentrated, then the residue was recrystallized from IPA/water to afford the title compound. $^1$H NMR (400 MHz, CDCl$_3$) δ 7.96 (m, 2H), 7.32 (m, 2H), 7.26 (m, 2H), 7.22 (m, 2H), 4.76 (dd, J=7.7, 2.9 Hz, 1H), 2.89 (ddd, J=11.5, 7.7, 4.2 Hz, 1H), 1.84 (d, J=2.9 Hz, 1H), 1.62 (s, 9H), 1.61 (m, 1H), 1.41 (m, 1H), 1.05 (m, 2H), 0.76 (t, J=7.3 Hz, 3H); LC3: 2.38 min. (M-H$_2$O-tBu+H)$^+$ 301; Chiral SFC Method: Chiralpak AD-H (250×4.6 mm), isocratic 15% MeOH/CO$_2$, 1.5 mL/min, 200 bar, 35° C., 215 nm, 15 minutes: desired alcohol retention time=9.8 min; enantiomeric alcohol, retention time=10.6 min; diastereomeric alcohols retention times=5.2 and 6.3 min.

Step C. 4-{(1R)-1-[(R)-(4-Chlorophenyl)(hydroxy)methyl]butyl}benzoic acid

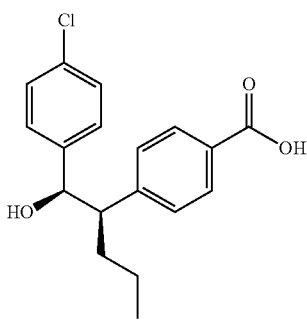 [SMILES: CCC[C@H](c1ccc(C(=O)O)cc1)[C@@H](O)c1ccc(Cl)cc1]

Orthophosphoric acid (85 wt %, 11.4 g, 99 mmol) was added to a slurry of tert-butyl 4-[(1R,2R)-2-(4-chlorophenyl)-1-propylethan-2-hydroxyl-1-yl]benzoate (7.42 g, 19.8 mmol) in acetonitrile (75 mL). The mixture was purged with nitrogen, then heated at 65° C. for 3.5 hours. The mixture was allowed to cool to 40° C., then water (25 mL) was added dropwise. Once crystallization began, additional water (50 mL) was added and the mixture was allowed to cool to room temperature. The precipitate was collected by vacuum filtration, washed with 3:1 water:acetonitrile (35 mL), then dried in vacuo at 65° C. overnight to afford the title compound as a light green solid. $^1$H NMR (400 MHz, DMSO-d$_6$) δ 12.71 (br s, 1H); 7.79 (d, J=8.3 Hz, 2H); 7.29 (d, J=8.4 Hz, 2H); 7.19-7.25 (m, 4H); 5.32 (br s, 1H); 4.76 (d, J=6.3 Hz, 1H); 2.85 (dt, J=10.7, 5.4 Hz, 1H); 1.61 (m, 1H); 1.44 (m, 1H); 1.00 (m, 2H); 0.73 (t, J=7.3 Hz, 3H)); LC2 3.00 min. (M+H)$^+$ 317.

Intermediate 2

7-BROMO-5-CHLORO-1-BENZOTHIOPHENE

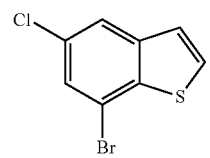 [SMILES: Clc1cc(Br)c2sccc2c1]

Step A.
2-Bromo-1[(2,2-diethoxyethyl)thio]-4-chlorobenzene

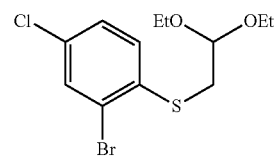 [SMILES: CCOC(CSc1ccc(Cl)cc1Br)OCC]

Potassium carbonate (0.926 g, 9.34 mmol) then bromoacetaldehyde dimethyl acetal (1.35 g, 6.85 mmol) were added to a solution of 2-bromo-4-chlorobenzenethiol (1.397 g, 6.23 mmol) in anhydrous DMF (11 mL). The mixture was heated at 70° C. for 3 hours. After being allowed to cool to room temperature, the mixture was diluted with ethyl acetate and water. The resulting layers were separated and the aqueous phase was extracted with ethyl acetate. The combined organics were washed with water then saturated NaCl (aq), dried over Na$_2$SO$_4$, filtered, then concentrated. The resulting light yellow oil was used directly for the following step. $^1$H NMR (500 MHz, CDCl$_3$) δ 7.57 (d, J=2.0 Hz, 1H); 7.33 (d, J=8.5 Hz, 1H); 7.26 (dd, J=8.5, 2.0 Hz, 1H); 4.70 (t, J=5.5 Hz, 1H); 3.75-3.68 (m, 2H); 3.61-3.55 (m, 2H); 3.15 (d, J=5.5 Hz, 2H); 1.23 (t, 7.0 Hz, 6H).

Step B. 7-Bromo-5-chloro-1-benzothiophene

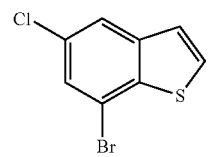 [SMILES: Clc1cc(Br)c2sccc2c1]

In a round-bottomed flask fitted with a reflux condenser and addition funnel, a mixture of chlorobenzene (11 mL) and polyphosphoric acid (7 g) was heated to reflux. A solution of 2-bromo-1-[(2,2-diethoxyethyl)thio]-4-chlorobenzene in chlorobenzene (10 mL) was added dropwise via addition funnel then the mixture was refluxed overnight. The viscous mixture was decanted while hot. Additional chlorobenzene (25 mL) was added to the flask, stirred at 120° C. for 15 minutes, then decanted. The remaining viscous mixture in the flask was treated with toluene (50 mL), water (25 mL), and saturated $Na_2CO_3$ (aq) (10 mL). The resulting layers were separated, and the aqueous phase was extracted with toluene. The toluene and chlorobenzene fractions were combined, washed with saturated $Na_2CO_3$ (aq), then saturated NaCl (aq), dried over $Na_2SO_4$, filtered, then concentrated. The residue was purified by silica gel chromatography eluting with 0-10% EtOAc/hexanes to afford the title compound as a white solid. $^1$H NMR (500 MHz, $CDCl_3$) δ 7.78 (d, J=1.5 Hz, 1H); 7.59 (d, J=5.5 Hz, 1H); 7.53 (d, J=1.5 Hz, 1H); 7.39 (d, J=5.5 Hz, 1H).

Intermediate 3

7-BROMO-5-(TRIFLUOROMETHYL)-1-BENZOTHIOPHENE

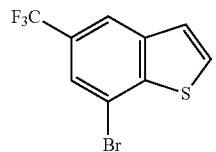 [SMILES: FC(F)(F)c1cc(Br)c2sccc2c1]

Step A.
3-Bromo-2-fluoro-5-(trifluoromethyl)benzaldehyde

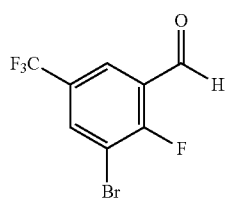 [SMILES: O=Cc1cc(C(F)(F)F)cc(Br)c1F]

A solution of n-BuLi (2.5 M in hexanes, 1.98 mL, 4.94 mmol) was added to a solution of diisopropylamine (0.700 mL, 4.94 mmol) in THF (10 mL) at −30° C. After 15 minutes, the mixture was cooled to −70° C., then 3-bromo-4-fluorobenzotrifluoride (1.00 g, 4.12 mmol) was added. After 30 minutes, anhydrous DMF (0.637 mL, 8.23 mmol) was added dropwise. After 15 minutes, acetic acid (0.50 mL, 8.2 mmol) was added, then the mixture was diluted with ethyl acetate and water. The resulting layers were separated, and the aqueous phase was extracted with ethyl acetate. The combined organics were washed with saturated NaCl (aq), dried over $Na_2SO_4$, filtered, then concentrated. The resulting light yellow oil was used directly for the following step. $^1$H NMR (500 MHz, $CDCl_3$) δ 10.38 (s, 1H); 8.10-8.15 (m, 2H). LC1: 3.44 min. Compound does not ionize.

Step B. Methyl 7-bromo-5-(trifluoromethyl)-1-benzothiophene-2-carboxylate

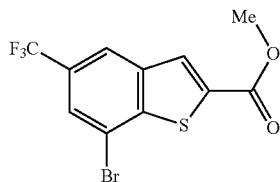 [SMILES: COC(=O)c1cc2cc(C(F)(F)F)cc(Br)c2s1]

Potassium carbonate (1.44 g, 10.42 mmol) then methyl thioglycolate (0.487 g, 4.59 mmol) were added to a degassed solution of 3-bromo-2-fluoro-5-(trifluoromethyl)benzaldehyde (1.13 g, 4.17 mmol) in $CH_3CN$ (11 mL). The mixture was stirred at room temperature for 30 minutes then refluxed at 100° C. overnight. The mixture was allowed to cool to room temperature, then water (20 mL) was added. The resulting light yellow solid was collected by vacuum filtration, washed with water, then dried in vacuo. The resulting ester was used directly for the following step. $^1$H NMR (500 MHz, $CDCl_3$) δ 8.24 (br s, 1H); 8.15 (br s, 1H); 7.86 (br s, 1H); 4.02 (br s, 3H). LC1: 4.00 min. Compound does not ionize.

Step C. 7-Bromo-5-(trifluoromethyl)-1-benzothiophene-2-carboxylic acid

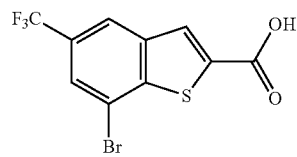 [SMILES: O=C(O)c1cc2cc(C(F)(F)F)cc(Br)c2s1]

A solution of NaOH (4.0 M in water, 5.0 mL, 20 mmol) was added to a solution of methyl 7-bromo-5-(trifluoromethyl)-1-benzothiophene-2-carboxylate (1.00 g, 2.95 mmol) in dioxane (11 mL). The mixture was heated at 70° C. overnight, allowed to cool to room temperature, then concentrated. The resulting light beige solid was partitioned between water (25 mL) and 1:1 hexanes:ethyl acetate (15 mL). The resulting layers were separated. The aqueous layer was adjusted to pH 2 with 2.0 M HCl (aq) then extracted four times with $CH_2Cl_2$. The combined $CH_2Cl_2$ layers were dried over $Na_2SO_4$, filtered, then concentrated. The resulting acid, a light yellow solid, was used directly for the following step. LC1: 3.58 min. Compound does not ionize.

Step D.
7-Bromo-5-(trifluoromethyl)-1-benzothiophene

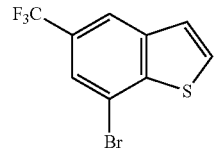 [SMILES: FC(F)(F)c1cc(Br)c2sccc2c1]

To a mixture of quinoline (5 mL) and copper powder (0.39 g, 6.2 mmol) in a sealed tube was added 7-bromo-5-(trifluoromethyl)-1-benzothiophene-2-carboxylic acid (1.0 g, 3.1 mmol). The mixture was heated to 200° C. for 20 minutes, then allowed to cool to room temperature. The mixture was filtered, then the collected precipitate was washed with toluene. The filtrate was concentrated, then the resulting brown oil was diluted with EtOAc and poured into 6.0 M HCl (aq). The layers were separated, then the aqueous layer was extracted with ethyl acetate. The combined organic layers were washed with 6.0 M HCl (aq), water, then saturated NaCl (aq), dried over $Na_2SO_4$, filtered, then concentrated. The residue was purified by silica gel chromatography eluting with 0-1% EtOAc/hexanes to afford the title compound as a colorless oil. $^1$H NMR (500 MHz, $CDCl_3$) δ 8.10 (br s, 1H); 7.77 (br s, 1H); 7.69 (d, J=5.5 Hz, 1H); 7.57 (d, J=5.5 Hz, 1H). LC1: 4.02 min. Compound does not ionize.

Example 1

N-(4-{(1S)-1-[(5-CHLORO-7-CYANO-1-BENZOTHIEN-3-YL)(4-CHLOROPHENYL)METHYL]BUTYL}BENZOYL)-β-ALANINE

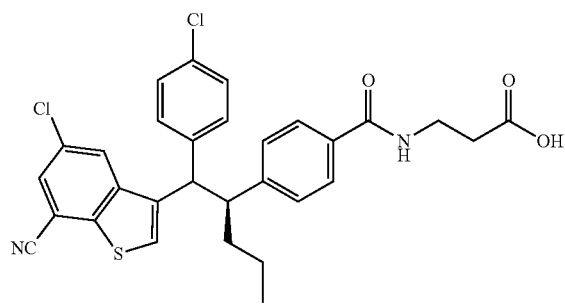 [SMILES: CCC[C@H](c1ccc(C(=O)NCCC(=O)O)cc1)C(c1ccc(Cl)cc1)c1csc2c(C#N)cc(Cl)cc12]

Step A. Ethyl N-(4-{(1S)-1-[(7-bromo-5-chloro-1-benzothien-3-yl)(4-chlorophenyl)methyl]butyl}benzoyl)-β-alaninate

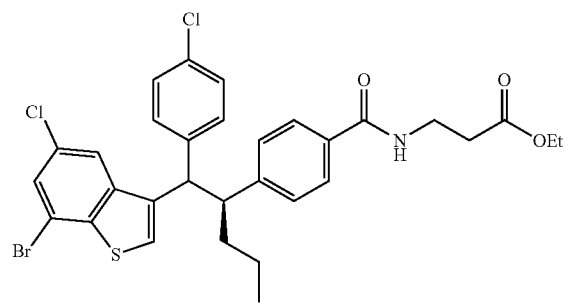 [SMILES: CCC[C@H](c1ccc(C(=O)NCCC(=O)OCC)cc1)C(c1ccc(Cl)cc1)c1csc2c(Br)cc(Cl)cc12]

Boron trifluoride diethyl etherate (0.88 mL, 7.0 mmol) was added dropwise to a solution of INTERMEDIATE 1 (0.400 g, 1.255 mmol) and INTERMEDIATE 2 (0.311 g, 1.255 mmol) in anhydrous dichloromethane (6.5 mL) at 0° C. The mixture was stirred at 0° C. for 5 minutes then at room temperature overnight. The mixture was diluted with EtOAc then washed with water. The aqueous phase was extracted with EtOAc. The combined organics were washed with saturated NaCl (aq), dried over $Na_2SO_4$, filtered, then concentrated. The resulting acid, a fluffy brown solid, was used directly for the following step. LC1: 4.34 min. (M−H)⁻ 545.

To a solution of the product from the previous step in THF (7.3 mL) was added N,N'-carbonyldiimidazole (1.017 g, 6.27 mmol). The mixture was stirred at room temperature for one hour, then β-alanine ethyl ester hydrochloride (0.964 g, 6.27 mmol) was added, and the mixture was stirred at 60° C. for 3 hours then at room temperature overnight. The mixture was concentrated, then the residue was purified by silica gel chromatography eluting with 30% EtOAc/hexanes. The resulting material was further purified by preparative HPLC (Daicel OD-H column, 2 cm×25 cm, 15% IPA/Heptane, 20 mL/min) to provide the title compound as a white solid. $^1$H NMR (500 MHz, $CDCl_3$) δ 7.62 (d, J=8 Hz, 2H); 7.57 (d, J=1.5 Hz, 1H); 7.42 (d, J=1.5 Hz, 1H); 7.30-7.35 (m, 5H); 7.27 (d, J=8 Hz, 2H); 6.76 (t, J=6 Hz, 1H); 4.47 (d, J=11 Hz, 1H); 4.20 (q, J=7 Hz, 2H); 3.71 (q, J=6 Hz, 2H); 3.47 (td, J=11, 3.5 Hz, 1H); 2.64 (t, J=5.5 Hz, 2H); 1.31 (t, J=7 Hz, 3H); 1.44-1.56 (m, 2H); 0.99-1.08 (m, 2H); 0.77 (t, J=7 Hz, 3H). LC1: 4.34 min. (M+H)⁺ 646.

Step B. Ethyl N-(4-{(1S)-1-[(5-chloro-7-cyano-1-benzothien-3-yl)(4-chlorophenyl)methyl]butyl}benzoyl)-β-alaninate

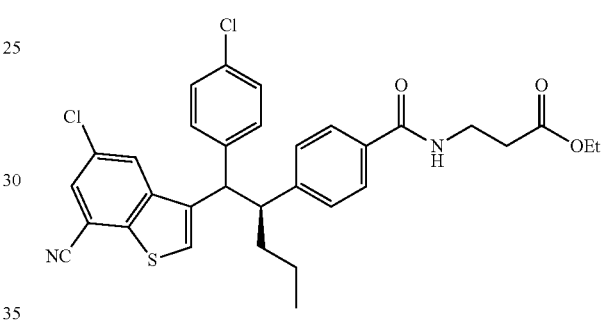

A degassed mixture of ethyl N-(4-{(1S)-1-[(7-bromo-5-chloro-1-benzothien-3-yl)(4-chlorophenyl)methyl]butyl}benzoyl)-β-alaninate (0.128 g, 0.198 mmol), zinc cyanide (0.046 g, 0.40 mmol) and tetrakis(triphenylphosphine)palladium(0) (0.114 g, 0.099 mmol) in anhydrous DMF (2.9 mL) was heated at 80° C. for 2.5 hours. After cooling to room temperature, the solution was concentrated, then the residue was purified by silica gel chromatography eluting with 35% EtOAc/hexanes. The resulting material was further purified by preparative HPLC (Daicel AD-H chiral column, 2 cm×25 cm, 16% IPA/Heptane, 20 mL/min) to provide the title compound as a white solid. LC1: 4.12 min. (M+H)⁺ 593.

Step C. N-(4-{(1S)-1-[(5-Chloro-7-cyano-1-benzothien-3-yl)(4-chlorophenyl)methyl]butyl}benzoyl)-β-alanine

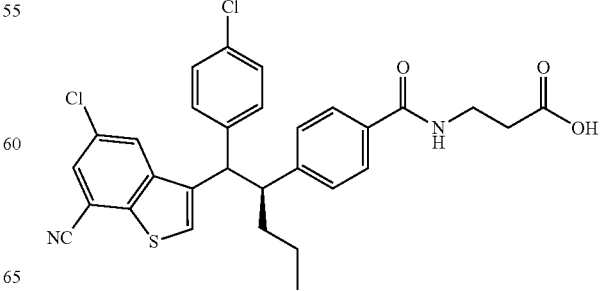

A solution of LiOH (2.0 M in water, 4.5 mL, 9.0 mmol) was added to a solution of ethyl N-(4-{(1S)-1-[(5-chloro-7-cyano-1-benzothien-3-yl)(4-chlorophenyl)methyl]butyl}benzoyl)-β-alaninate (0.100 g, 0.168 mmol) in THF (9.0 mL). The mixture was stirred at room temperature for four hours then acidified with acetic acid and extracted with ethyl acetate. The organics were dried over Na₂SO₄, filtered, then concentrated. The resulting residue was purified by reverse-phase HPLC eluting with 20-100% acetonitrile/water containing 0.1% TFA. Following lyophilization, the material was further purified by silica gel chromatography eluting with 5% MeOH in DCM containing 0.5% acetic acid to afford the title compound as a white solid. $^1$H NMR (500 MHz, CDCl₃) δ 7.77 (br s, 1H); 7.60 (d, J=5 Hz, 2H); 7.52 (br s, 1H); 7.42 (br s, 1H); 7.31-7.35 (m, 4H); 7.25 (d, J=7 Hz, 2H); 6.78 (br s, 1H); 4.49 (d, J=11 Hz, 1H); 3.67 (br s, 2H); 3.44-3.47 (m, 1H); 2.66 (br, 2H); 1.45-1.53 (m, 2H); 0.98-1.05 (m, 2H); 0.73 (t, J=7 Hz, 3H). LC1: 3.97 min. (M+H)⁺ 565.

Example 2

N-[4-((1S)-1-{(4-CHLOROPHENYL)[5-FLUORO-7-(1-METHYL-1H-PYRAZOL-5-YL)-1-BENZOTHIEN-3-YL]METHYL}PENTYL)BENZOYL]-β-ALANINE

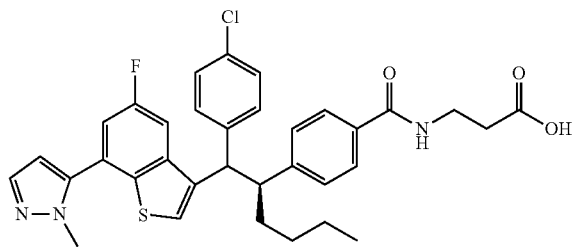 [SMILES: CCCC[C@H](c1ccc(C(=O)NCCC(=O)O)cc1)C(c1ccc(Cl)cc1)c1csc2c(-c3ccnn3C)cc(F)cc12]

Step A. Ethyl N-(4-{(1S)-1-[(7-bromo-5-fluoro-1-benzothien-3-yl)(4-chlorophenyl)methyl]pentyl}benzoyl)-β-alaninate

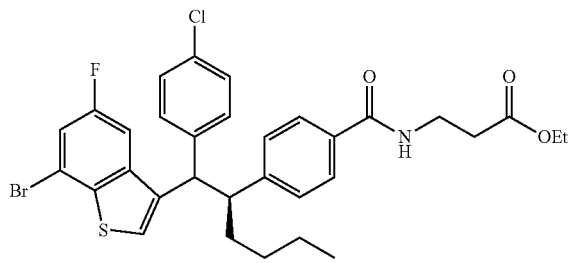 [SMILES: CCCC[C@H](c1ccc(C(=O)NCCC(=O)OCC)cc1)C(c1ccc(Cl)cc1)c1csc2c(Br)cc(F)cc12]

Using the procedures from INTERMEDIATES 1 and 2 and EXAMPLE 1, 1-(4-chlorophenyl)hexan-1-one and 2-bromo-4-fluorobenzenethiol were converted to the title compound. $^1$H NMR (500 MHz, CDCl₃): δ 7.62 (d, J=8 Hz, 2H); 7.37 (br, 1H); 7.30-7.35 (m, 6H); 7.27 (d, J=8 Hz, 2H); 6.76 (t, J=6 Hz, 1H); 4.45 (d, J=11 Hz, 1H); 4.19 (q, J=7 Hz, 2H); 3.71 (q, J=6 Hz, 2H); 3.46 (t, J=10.5 Hz, 1H); 2.64 (t, J=5.5 Hz, 2H); 1.30 (t, J=7 Hz, 3H); 1.47-1.57 (m, 2H); 1.18-1.23 (m, 1H); 1.07-1.14 (m, 1H); 0.98-1.03 (m, 2H); 0.75 (t, J=7 Hz, 3H). LC1: 4.23 min. (M+H)⁺ 644 and 646.

Step B. N-[4-((1S)-1-{(4-Chlorophenyl)[5-fluoro-7-(1-methyl-1H-pyrazol-5-yl)-1-benzothien-3-yl]methyl}pentyl)benzoyl]-β-alanine

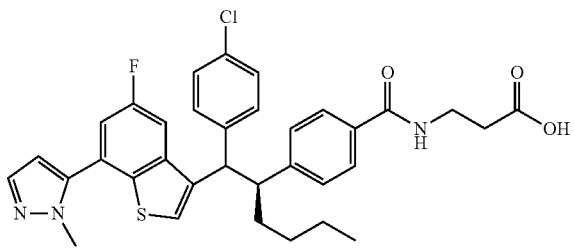 [SMILES: CCCC[C@H](c1ccc(C(=O)NCCC(=O)O)cc1)C(c1ccc(Cl)cc1)c1csc2c(-c3ccnn3C)cc(F)cc12]

Dioxane (1.4 mL) and LiOH (2.0 M in water, 0.68 mL, 1.36 mmol) were added to a mixture of ethyl N-(4-{(1S)-1-[(7-bromo-5-fluoro-1-benzothien-3-yl)(4-chlorophenyl)methyl]pentyl}benzoyl)-β-alaninate (23.0 mg, 0.036 mmol), 1-methyl-1H-pyrazole-5-boronic acid pinacol ester (11.0 mg, 0.053 mmol), and PdCl₂(dppf) (0.029 g, 0.036 mmol) in a sealed microwave vial under a nitrogen atmosphere. The mixture was degassed then irradiated in a microwave reactor at 80° C. for 15 minutes. The mixture was acidified with acetic acid then extracted with ethyl acetate. The organic layer was dried over Na₂SO₄, filtered, then concentrated. The resulting residue was purified by preparative reverse-phase HPLC eluting with acetonitrile/water+0.1% TFA. The resulting material was further purified by silica gel chromatography eluting with 5% MeOH/DCM+0.5% acetic acid to afford the title compound. $^1$H NMR (500 MHz, CDCl₃): δ 7.57 (br, 3H); 7.29-7.37 (m, 6H); 7.23 (d, J=6 Hz, 2H); 6.94 (d, J=7 Hz, 1H); 6.86 (br, 1H); 6.40 (br, 1H); 4.47 (d, J=11 Hz, 1H); 3.71 (br, 3H); 3.62 (br, 2H); 3.43 (t, J=9.5 Hz, 1H); 2.59 (br, 2H); 1.45-1.52 (m, 2H); 1.13-1.16 (m, 1H); 1.04-1.06 (m, 1H); 0.88-1.00 (m, 2H); 0.68 (t, J=6.5 Hz, 3H). LC1: 3.99 min. (M+H)⁺ 618.

Example 3

4-{(1S)-1-[(7-BROMO-5-METHYL-1-BENZOTHIEN-3-YL)(4-CHLOROPHENYL)METHYL]BUTYL}-N-1H-TETRAZOL-5-YLBENZAMIDE

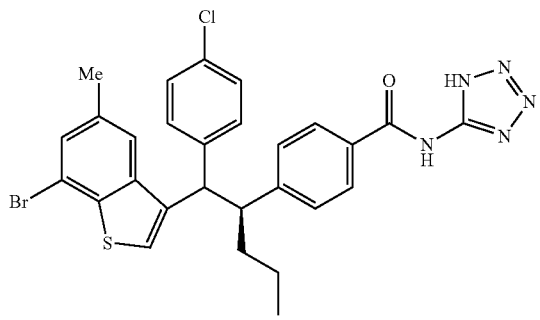 [SMILES: CCC[C@H](c1ccc(C(=O)Nc2nnn[nH]2)cc1)C(c1ccc(Cl)cc1)c1csc2c(Br)cc(C)cc12]

Step A. 4-{(1S)-1-[(7-Bromo-5-methyl-1-benzothien-3-yl)(4-chlorophenyl)methyl]butyl}benzoic acid

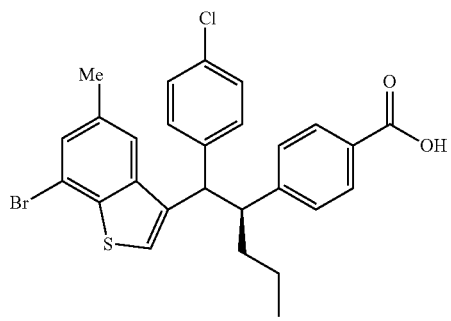 [SMILES: CCC[C@H](c1ccc(C(=O)O)cc1)C(c1ccc(Cl)cc1)c1csc2c(Br)cc(C)cc12]

Using the procedures from INTERMEDIATE 2 and EXAMPLE 1, 2-bromo-4-methylbenzenethiol and INTERMEDIATE 1 were converted to the title compound. LC2: 2.82 min. Compound does not ionize.

Step B. 4-{(1S)-1-[(7-Bromo-5-methyl-1-benzothien-3-yl)(4-chlorophenyl)methyl]butyl}-N-1H-tetrazol-5-ylbenzamide

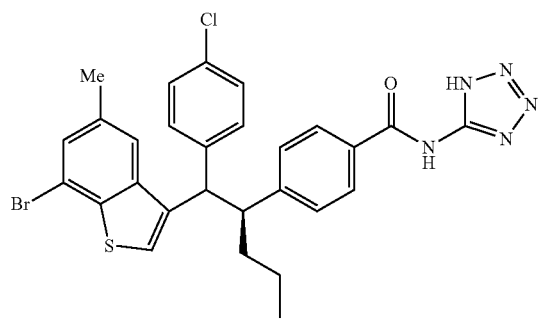 [SMILES: CCC[C@H](c1ccc(C(=O)Nc2nnn[nH]2)cc1)C(c1ccc(Cl)cc1)c1csc2c(Br)cc(C)cc12]

A mixture of 4-{(1S)-1-[(7-bromo-5-methyl-1-benzothien-3-yl)(4-chlorophenyl)methyl]butyl}benzoic acid (25.0 mg, 0.047 mmol) and CDI (26 mg, 0.16 mmol) in DMF (1.0 mL) was stirred at RT for 30 minutes in a sealed tube, then 5-amino-1H-tetrazole (23.0 mg, 0.260 mmol) was added. The mixture was heated at 100° C. for 12 hours, allowed to cool to RT, then diluted with acetonitrile. The mixture was purified by preparative reverse phase HPLC eluting with 47-100% acetonitrile/water+0.1% TFA. Following lyophilization, this afforded the title compound as a white solid. $^1$H NMR (500 MHz, $d_6$-DMSO) δ 7.98 (br, 1H); 7.91 (d, J=8 Hz, 2H); 7.84 (br, 1H); 7.65 (d, J=8 Hz, 2H); 7.61 (d, J=8 Hz, 2H); 7.39 (d, J=8.5 Hz, 2H); 7.35 (br, 1H); 4.88 (d, J=12 Hz, 1H); 3.79 (t, J=11 Hz, 1H); 2.41 (s, 3H); 1.50-1.52 (m, 1H); 1.23-1.30 (m, 1H); 0.92 (q, J=7 Hz, 2H); 0.68 (t, J=7 Hz, 3H). LC2: 2.70 min. (M+H)$^+$ 594.

Example 4

4-{(1S)-1-[(7-BROMO-5-METHYL-1-BENZOTHIEN-3-YL)(4-CHLOROPHENYL)METHYL]BUTYL}-N-(2H-TETRAZOL-5-YLMETHYL)BENZAMIDE

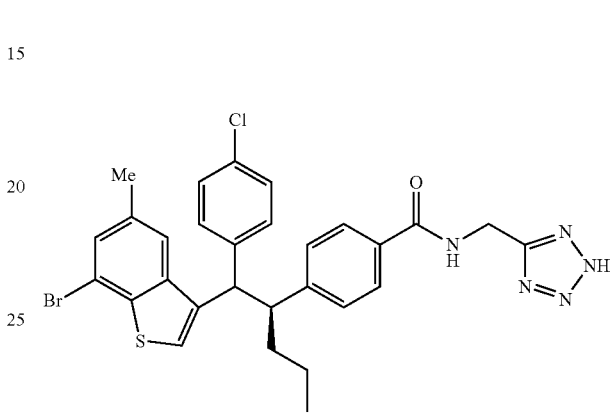

A mixture of 4-{(1S)-1-[(7-bromo-5-methyl-1-benzothien-3-yl)(4-chlorophenyl)methyl]butyl}benzoic acid (EXAMPLE 3, Step A, 20.0 mg, 0.038 mmol), 1-(2H-tetrazol-5-yl)methanamine (10.9 mg, 0.110 mmol), EDC (22.0 mg, 0.110 mmol), HOBt (17.0 mg, 0.110 mmol) and DIEA (0.050 mL, 0.29 mmol) in DMF (1 mL) was heated at 65° C. for 12 hours. The mixture was allowed to cool to RT, diluted with acetonitrile, then purified by preparative reverse-phase HPLC eluting with 38-100% acetonitrile/water+0.1% TFA. Following lyophilization, this afforded the title compound as a white solid. $^1$H NMR (500 MHz, $d_6$-DMSO) δ 9.04 (br, 1H); 7.96 (s, 1H); 7.84 (s, 1H); 7.67 (d, J=8 Hz, 2H); 7.64 (d, J=8 Hz, 2H); 7.52 (d, J=8 Hz, 2H); 7.39 (d, J=8.5 Hz, 2H); 7.35 (br, 1H); 4.84 (d, J=11.5 Hz, 1H); 4.67 (d, J=5.5 Hz, 2H); 3.74 (t, J=12 Hz, 1H); 2.40 (s, 3H); 1.44-1.52 (m, 1H); 1.24-1.32 (m, 1H); 0.91 (q, J=7.5 Hz, 2H); 0.67 (t, J=7 Hz, 3H). LC2: 2.63 min. (M+H)$^+$ 608.

Using the chemistry described for the preparation of INTERMEDIATES 1-3 and in EXAMPLES 1-4, the compounds in TABLES 1 and 3 were prepared as enantiopure compounds. The data listed are for the most active stereoisomer. Most compounds in TABLE 2 were also prepared as single stereoisomers, with the data listed being that for the most active stereoisomer. The only exceptions are examples 41 and 42, in which the compounds are a mixture of the two possible diastereomers at the stereocenter on the substituent labeled "Y" in the general structure. The $R^1$ and $R^3$ groups that are shown in TABLES 1-3 are specified when they represent a value other than a hydrogen atom. The remaining $R^1$ and $R^3$ groups that are unspecified are hydrogen atoms.

TABLE 1

| EXAMPLE | R¹ | R² | R³ | LC-MS data |
|---|---|---|---|---|
| 5 | 4-Cl | n-Pr | H | LC1 3.87 min. (M + H)⁺ 506.5 |
| | N-(4-{(1S)-1-[1-BENZOTHIEN-3-YL(4-CHLOROPHENYL)METHYL]BUTYL}BENZOYL)-β-ALANINE | | | |
| 6 | 4-Cl | n-Pr | 5-Cl, 7-Me | LC1 4.08 min. (M + H)⁺ 552 |
| | N-(4-{(1S)-1-[(5-CHLORO-7-METHYL-1-BENZOTHIEN-3-YL)(4-CHLOROPHENYL)METHYL]BUTYL}BENZOYL)-β-ALANINE | | | |
| 7 | 4-Cl | n-Pr | 5-Cl, 7-Br | LC1 4.26 min. (M + H)⁺ 618.6 |
| | N-(4-{(1S)-1-[(5-CHLORO-7-BROMO-1-BENZOTHIEN-3-YL)(4-CHLOROPHENYL)METHYL]BUTYL}BENZOYL)-β-ALANINE | | | |
| 8 | 4-Cl | n-Pr | 2-Me | LC1 4.02 min. (M + H)⁺ 520.6 |
| | N-(4-{(1S)-1-[(2-METHYL-1-BENZOTHIEN-3-YL)(4-CHLOROPHENYL)METHYL]BUTYL}BENZOYL)-β-ALANINE | | | |
| 9 | 4-Cl | n-Pr | 5-F, 7-Cl | LC1 4.13 min. (M + H)⁺ 558 |
| | N-(4-{(1S)-1-[(5-FLUORO-7-CHLORO-1-BENZOTHIEN-3-YL)(4-CHLOROPHENYL)METHYL]BUTYL}BENZOYL)-β-ALANINE | | | |
| 10 | 4-OMe | n-Pr | H | LC1 3.62 min. (M + H)⁺ 502 |
| | N-(4-{(1S)-1-[1-BENZOTHIEN-3-YL(4-METHOXYPHENYL)METHYL]BUTYL}BENZOYL)-β-ALANINE | | | |
| 11 | 3,4-diCl | n-Pr | 5-Cl | LC2 2.48 min. (M + H)⁺ 576 |
| | N-(4-{(1S)-1-[(5-CHLORO-1-BENZOTHIEN-3-YL)(3,4-DICHLOROPHENYL)METHYL]BUTYL}BENZOYL)-β-ALANINE | | | |
| 12 | 3,4-diCl | n-Pr | 5-Cl, 7-Br | LC2 2.66 min. (M + H)⁺ 654 |
| | N-(4-{(1S)-1-[(5-CHLORO-7-BROMO-1-BENZOTHIEN-3-YL)(3,4-DICHLOROPHENYL)METHYL]BUTYL}BENZOYL)-β-ALANINE | | | |
| 13 | 4-Cl | n-Pr | 5-F, 7-CN | LC1 3.95 min. (M + H)⁺ 549 |
| | N-(4-{(1S)-1-[(5-FLUORO-7-CYANO-1-BENZOTHIEN-3-YL)(4-CHLOROPHENYL)METHYL]BUTYL}BENZOYL)-β-ALANINE | | | |
| 14 | 4-Cl | n-Pr | 5-Me, 7-CN | LC1 3.99 min. (M + H)⁺ 545 |
| | N-(4-{(1S)-1-[(5-METHYL-7-CYANO-1-BENZOTHIEN-3-YL)(4-CHLOROPHENYL)METHYL]BUTYL}BENZOYL)-β-ALANINE | | | |
| 15 | 4-Cl | n-Pr | 5-CF₃, 7-CN | LC1 4.01 min. (M + H)⁺ 599 |
| | N-(4-{(1S)-1-[(5-TRIFLUOROMETHYL-7-CYANO-1-BENZOTHIEN-3-YL)(4-CHLOROPHENYL)METHYL]BUTYL}BENZOYL)-β-ALANINE | | | |
| 16 | 4-Cl | n-Pr | 5,6-diF, 7-CN | LC1 3.94 min. (M + H)⁺ 567 |
| | N-(4-{(1S)-1-[(5,6-DIFLUORO-7-CYANO-1-BENZOTHIEN-3-YL)(4-CHLOROPHENYL)METHYL]BUTYL}BENZOYL)-β-ALANINE | | | |
| 17 | 4-Cl | n-Pr | 4,5-diF, 7-CN | LC1 3.99 min. (M + H)⁺ 567 |
| | N-(4-{(1S)-1-[(4,5-DIFLUORO-7-CYANO-1-BENZOTHIEN-3-YL)(4-CHLOROPHENYL)METHYL]BUTYL}BENZOYL)-β-ALANINE | | | |
| 18 | 4-Cl | n-Pr | 2-Me, 5-F, 7-CN | LC1 3.99 min. (M + H)⁺ 563 |
| | N-(4-{(1S)-1-[(2-METHYL-5-FLUORO-7-CYANO-1-BENZOTHIEN-3-YL)(4-CHLOROPHENYL)METHYL]BUTYL}BENZOYL)-β-ALANINE | | | |
| 19 | 4-Cl | n-Pr | 2-Me, 5-Cl, 7-CN | LC1 4.06 min. (M + H)⁺ 577 |
| | N-(4-{(1S)-1-[(2-METHYL-5-CHLORO-7-CYANO-1-BENZOTHIEN-3-YL)(4-CHLOROPHENYL)METHYL]BUTYL}BENZOYL)-β-ALANINE | | | |
| 20 | 3,5-diF | n-Pr | 5-CF₃, 7-CN | LC1 3.94 min. (M + H)⁺ 601 |
| | N-(4-{(1S)-1-[(5-TRIFLUOROMETHYL-7-CYANO-1-BENZOTHIEN-3-YL)(3,5-DIFLUOROPHENYL)METHYL]BUTYL}BENZOYL)-β-ALANINE | | | |
| 21 | 3,4-diCl | n-Pr | 5-Cl, 7-CN | LC2 2.31 min. (M + H)⁺ 601 |
| | N-(4-{(1S)-1-[(5-CHLORO-7-CYANO-1-BENZOTHIEN-3-YL)(3,4-DICHLOROPHENYL)METHYL]BUTYL}BENZOYL)-β-ALANINE | | | |
| 22 | 4-OCF₃ | n-Pr | 5-F, 7-CN | LC1 3.98 min. (M + H)⁺ 599 |
| | N-(4-{(1S)-1-[(5-FLUORO-7-CYANO-1-BENZOTHIEN-3-YL)(4-TRIFLUOROMETHOXYPHENYL)METHYL]BUTYL}BENZOYL)-β-ALANINE | | | |
| 23 | 4-OCF₃ | n-Pr | 5-Me, 7-CN | LC2 2.62 min. (M + H)⁺ 595 |
| | N-(4-{(1S)-1-[(5-METHYL-7-CYANO-1-BENZOTHIEN-3-YL)(4-TRIFLUOROMETHOXYPHENYL)METHYL]BUTYL}BENZOYL)-β-ALANINE | | | |
| 24 | 4-OCF₃ | n-Pr | 5-CF₃, 7-CN | LC1 4.04 min. (M + H)⁺ 649 |
| | N-(4-{(1S)-1-[(5-TRIFLUOROMETHYL-7-CYANO-1-BENZOTHIEN-3-YL)(4-TRIFLUOROMETHOXYPHENYL)METHYL]BUTYL}BENZOYL)-β-ALANINE | | | |
| 25 | 4-OCF₃ | n-Pr | 5-Cl, 7-CN | LC2 2.67 min. (M + H)⁺ 615 |
| | N-(4-{(1S)-1-[(5-CHLORO-7-CYANO-1-BENZOTHIEN-3-YL)(4-TRIFLUOROMETHOXYPHENYL)METHYL]BUTYL}BENZOYL)-β-ALANINE | | | |

TABLE 1-continued

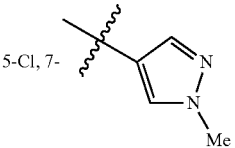 [SMILES: *c1cnn(C)c1]

| EXAMPLE | R¹ | R² | R³ | LC-MS data |
|---|---|---|---|---|
| 26 | 4-OCF₃ | n-Pr | 5,6-diF, 7-CN | LC2 2.65 min. (M + H)⁺ 617 |
| | N-(4-{(1S)-1-[(5,6-DIFLUORO-7-CYANO-1-BENZOTHIEN-3-YL)(4-TRIFLUOROMETHOXYPHENYL)METHYL]BUTYL}BENZOYL)-β-ALANINE | | | |
| 27 | 4-Cl | —CH₂CH₂CF₃ | 5-Cl, 7-CN | LC1 3.91 min. (M + H)⁺ 619 |
| | N-(4-{(1S)-1-[(5-CHLORO-7-CYANO-1-BENZOTHIEN-3-YL)(4-CHLOROPHENYL)METHYL]-4,4,4-TRIFLUOROBUTYL}BENZOYL)-β-ALANINE | | | |
| 28 | 4-Cl | —CH₂CH₂CF₃ | 5-Me, 7-CN | LC2 2.53 min. (M + H)⁺ 599 |
| | N-(4-{(1S)-1-[(5-METHYL-7-CYANO-1-BENZOTHIEN-3-YL)(4-CHLOROPHENYL)METHYL]-4,4,4-TRIFLUOROBUTYL}BENZOYL)-β-ALANINE | | | |
| 29 | 4-Cl | n-Bu | 5-Cl, 7-CN | LC1 4.13 min. (M + H)⁺ 579 |
| | N-(4-{(1S)-1-[(5-CHLORO-7-CYANO-1-BENZOTHIEN-3-YL)(4-CHLOROPHENYL)METHYL]PENTYL}BENZOYL)-β-ALANINE | | | |
| 30 | 4-Cl | n-Bu | 5-F, 7-CN | LC1 4.06 min. (M + H)⁺ 561 |
| | N-(4-{(1S)-1-[(5-FLUORO-7-CYANO-1-BENZOTHIEN-3-YL)(4-CHLOROPHENYL)METHYL]PENTYL}BENZOYL)-β-ALANINE | | | |
| 31 | 4-Cl | n-Bu | 5-CF₃, 7-CN | LC1 4.20 min. (M + H)⁺ 613 |
| | N-(4-{(1S)-1-[(5-TRIFLUOROMETHYL-7-CYANO-1-BENZOTHIEN-3-YL)(4-CHLOROPHENYL)METHYL]PENTYL}BENZOYL)-β-ALANINE | | | |
| 32 | 4-Cl | —CH₂CH(CH₃)₂ | 5-Cl, 7-CN | LC1 4.11 min. (M + H)⁺ 579 |
| | N-(4-{(1S)-1-[(5-CHLORO-7-CYANO-1-BENZOTHIEN-3-YL)(4-CHLOROPHENYL)METHYL]-4-METHYLBUTYL}BENZOYL)-β-ALANINE | | | |
| 33 | 4-Cl | —CH₂CH(CH₃)₂ | 5-F, 7-CN | LC1 4.03 min. (M + H)⁺ 563 |
| | N-(4-{(1S)-1-[(5-FLUORO-7-CYANO-1-BENZOTHIEN-3-YL)(4-CHLOROPHENYL)METHYL]-4-METHYLBUTYL}BENZOYL)-β-ALANINE | | | |
| 34 | 4-Cl | Et | 5-Cl, 7-CN | LC1 3.90 min. (M + H)⁺ 551 |
| | N-(4-{(1S)-1-[(5-CHLORO-7-CYANO-1-BENZOTHIEN-3-YL)(4-CHLOROPHENYL)METHYL]PROPYL}BENZOYL)-β-ALANINE | | | |
| 35 | 4-Cl | n-Pr | 5-Cl, 7- 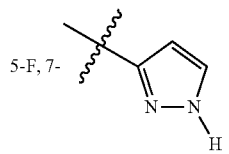 [SMILES: *c1cc[nH]n1] | LC1 3.93 min. (M + H)⁺ 620 |
| | N-[4-((1S)-1-{(4-CHLOROPHENYL)[5-CHLORO-7-(1-METHYL-1H-PYRAZOL-4-YL)-1-BENZOTHIEN-3-YL]METHYL}BUTYL)BENZOYL]-β-ALANINE | | | |
| 36 | 4-OCF₃ | n-Pr | 5-F, 7- 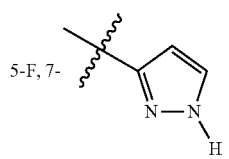 | LC1 3.86 min. (M + H)⁺ 640 |
| | N-[4-((1S)-1-{(4-TRIFLUOROMETHOXYPHENYL)[5-FLUORO-7-(1H-PYRAZOL-3-YL)-1-BENZOTHIEN-3-YL]METHYL}BUTYL)BENZOYL]-β-ALANINE | | | |
| 37 | 4-Cl | n-Bu | 5-F, 7- 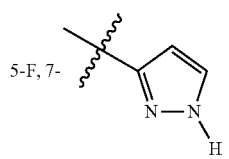 | LC1 3.93 min. (M + H)⁺ 604 |
| | N-[4-((1S)-1-{(4-CHLOROPHENYL)[5-FLUORO-7-(1H-PYRAZOL-3-YL)-1-BENZOTHIEN-3-YL]METHYL}PENTYL)BENZOYL]-β-ALANINE | | | |

TABLE 1-continued

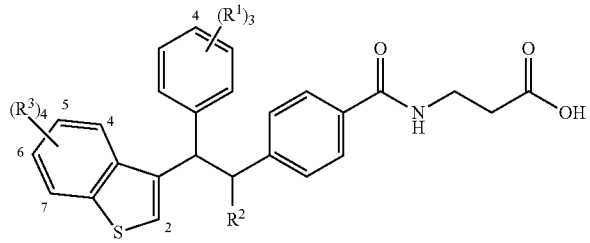

| EXAMPLE | R¹ | R² | R³ | LC-MS data |
|---|---|---|---|---|
| 38 | 4-Cl | n-Pr | 5-Cl, 7- 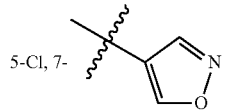 [SMILES: *c1cnoc1] | LC2 2.56 min. (M + H)⁺ 607 |

N-[4-((1S)-1-{(4-CHLOROPHENYL)[5-CHLORO-7-(1H-ISOXAZOL-4-YL)-1-BENZOTHIEN-3-YL]METHYL}BUTYL)BENZOYL]-β-ALANINE

TABLE 2

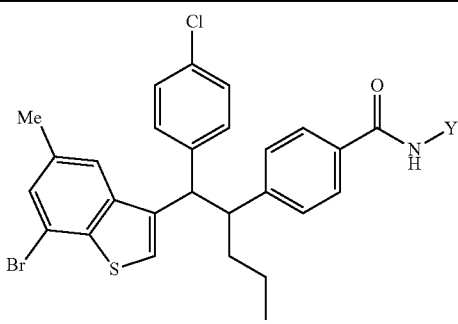

| EXAMPLE | Y | LC-MS data |
|---|---|---|
| 39 | 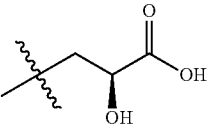 [SMILES: *C[C@H](O)C(=O)O] | LC3 2.59 min. (M + H)⁺ 614 |

(2S)-3-[(4-{(1S)-1-[(5-METHYL-7-BROMO-1-BENZOTHIOPHEN-3-YL)(4-CHLOROPHENYL)METHYL]BUTYL}BENZOYL)AMINO]-2-HYDROXYPROPANOIC ACID

| 40 | 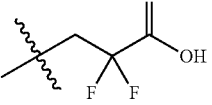 | LC3 2.63 min. (M + H)⁺ 634 |
|---|---|---|

3-[(4-{(1S)-1-[(5-METHYL-7-BROMO-1-BENZOTHIOPHEN-3-YL)(4-CHLOROPHENYL)METHYL]BUTYL}BENZOYL)AMINO]-2,2-DIFLUOROPROPANOIC ACID

| 41 | 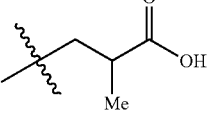 | LC3 2.70 min. (M + H)⁺ 612 |
|---|---|---|

3-[(4-{(1S)-1-[(5-METHYL-7-BROMO-1-BENZOTHIOPHEN-3-YL)(4-CHLOROPHENYL)METHYL]BUTYL}BENZOYL)AMINO]-2-METHYLPROPANOIC ACID

TABLE 2-continued

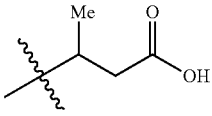 [SMILES: *C(C)CC(=O)O]

| EXAMPLE | Y | LC-MS data |
|---|---|---|
| 42 | 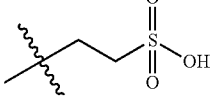 | LC3 2.69 min. (M + H)⁺ 612 |

3-[(4-{(1S)-1-[(5-METHYL-7-BROMO-1-BENZOTHIOPHEN-3-YL)(4-CHLOROPHENYL)METHYL]BUTYL}BENZOYL)AMINO]-3-METHYLPROPANOIC ACID

| 43 | 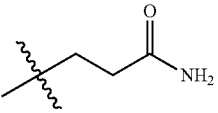 [SMILES: *CCC(N)=O] | LC3 2.36 min. (M + H)⁺ 634 |
|---|---|---|

2-[(4-{(1S)-1-[(5-METHYL-7-BROMO-1-BENZOTHIOPHEN-3-YL)(4-CHLOROPHENYL)METHYL]BUTYL}BENZOYL)AMINO]ETHANE SULFONIC ACID

| 44 | 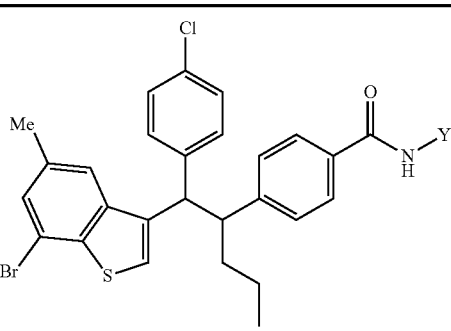 | LC3 2.57 min. (M + H)⁺ 597 |
|---|---|---|

3-[(4-{(1S)-1-[(5-METHYL-7-BROMO-1-BENZOTHIOPHEN-3-YL)(4-CHLOROPHENYL)METHYL]BUTYL}BENZOYL)AMINO] PROPANOIC AMIDE

TABLE 3

| EXAMPLE | R¹ | R² | R³ | LC-MS data |
|---|---|---|---|---|
| 45 | 4-Cl | n-Pr | H | LC1 4.07 min. (M + H)⁺ 520.6 |
| N-[4-((1S)-1-{(4-CHLOROPHENYL)[3-METHYL-1-BENZOTHIEN-2-YL]METHYL}BUTYL)BENZOYL]-β-ALANINE | | | | |
| 46 | 4-Cl | n-Pr | 5-Cl | LC1 4.19 min. (M + H)⁺ 554.6 |
| N-[4-((1S)-1-{(4-CHLOROPHENYL)[3-METHYL-5-CHLORO-1-BENZOTHIEN-2-YL]METHYL}BUTYL)BENZOYL]-β-ALANINE | | | | |
| 47 | 4-Cl | n-Pr | 7-Cl | LC1 4.22 min. (M + H)⁺ 554.5 |
| N-[4-((1S)-1-{(4-CHLOROPHENYL)[3-METHYL-7-CHLORO-1-BENZOTHIEN-2-YL]METHYL}BUTYL)BENZOYL]-β-ALANINE | | | | |
| 48 | 4-OMe | n-Pr | 5-Cl | LC1 3.91 min. (M + H)⁺ 550.6 |
| N-[4-((1S)-1-{(4-METHOXYPHENYL)[3-METHYL-5-CHLORO-1-BENZOTHIEN-2-YL]METHYL}BUTYL)BENZOYL]-β-ALANINE | | | | |

TABLE 4

| Example | IC$_{50}$ (nM) |
|---|---|
| 1 | 6.2 |
| 2 | 4.7 |
| 3 | 2.3 |
| 4 | 2.5 |
| 6 | 28 |
| 8 | 2.2 |
| 13 | 1.1 |
| 14 | 1.3 |
| 15 | 1.7 |
| 19 | 7.8 |
| 21 | 0.7 |
| 23 | 0.2 |
| 25 | 0.1 |
| 27 | 0.2 |
| 29 | 0.4 |
| 32 | 1.0 |
| 40 | 11.8 |
| 43 | 3.4 |
| 45 | 1.8 |

BIOLOGICAL ASSAYS

The ability of the compounds of the present invention to inhibit the binding of glucagon and their utility in treating or preventing type 2 diabetes mellitus and the related conditions can be demonstrated by the following in vitro assays.

Glucagon Receptor Binding Assay

A stable CHO (Chinese hamster ovary) cell line expressing cloned human glucagon receptor was maintained as described (Chicchi, et. al. *J Biol Chem* 272, 7765-9 (1997); Cascieri, et. al. *J Biol Chem* 274, 8694-7 (1999)). To determine antagonistic binding affinity of compounds, 0.001-0.003 mg of cell membranes from these cells were pre-incubated with 0.100 mg WGA-coated PVT SPA beads (Amersham) for 20 minutes at room temperature in 25 μL of a buffer containing 50 mM Tris-HCl (pH 7.5), 5 mM MgCl$_2$, 2 mM EDTA, 0.1% BSA and 3% glycerol in Costar 384 well plates with clear bottoms (#3706). Next, 25 μL of $^{125}$I-Glucagon (New England Nuclear, MA) (1×10$^{-14}$ mol per well) and either 1 μL solutions of test compounds or 0.001 mM unlabeled glucagon or DMSO were added and mixed. After 4-12 hours incubation at room temperature, the radioactivity bound to the cell membranes was determined in a radioactive emission detection counter (Wallac-Microbeta). Data were analyzed using the Data Analyzer software program of Merck & Co., Inc. The IC$_{50}$ values were calculated using non-linear regression analysis assuming single-site competition. IC$_{50}$ values for the compounds of the invention are generally in the range of as low as about 1 nM to as high as about 500 nM, and thus have utility as glucagon antagonists. The IC$_{50}$ values are shown below in TABLE 4 for the more active isomer of indicated compounds.

Inhibition of Glucagon-Stimulated Intracellular cAMP Formation

Exponentially growing CHO cells expressing human glucagon receptor were harvested with the aid of enzyme-free dissociation media (Specialty Media), pelleted at low speed, and re-suspended in the Cell Stimulation Buffer included in the Flash Plate cAMP kit (New England Nuclear, SMP0004A). The adenylate cyclase assay was conducted as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in the presence of compounds or DMSO controls for 30 minutes, then stimulated with glucagon (250 pM) for an additional 30 minutes. The cell stimulation was stopped by addition of equal amounts of a detection buffer containing lysis buffer as well as $^{125}$I-labeled cAMP tracer (NEN). After 3 hours of incubation at room temperature the bound radioactivity was determined in a liquid scintillation counter (TopCount-Packard Instruments). Basal activity (100% inhibition) was determined using the DMSO control while 0% inhibition was defined at the amount of pmol cAMP produced by 250 pM glucagon. The resulting amount of cAMP generated per compound dose was back-calculated from a cAMP standard curve based on the percent inhibition achieved at each dose. The calculated cAMP levels were plotted versus compound dose to obtain IC$_{50}$ values using non-linear four-parameter curve fitting with Assay Data Analyzer software (Merck & Co., Inc.).

Certain embodiments of the invention have been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:

1. A compound represented by formula I:

I

![Formula I structure showing (R¹)₃ on phenyl, (R³)₄ on benzothiophene with S, central carbons bearing R², connected to phenyl-C(O)NH(C(R⁴)₂)ₘ-Z]

or a pharmaceutically acceptable salt thereof wherein:
  each $R^1$ represents H or is selected from the group consisting of halo, $C_{1-10}$alkyl, or $C_{1-10}$alkoxy, the alkyl portions of $C_{1-10}$alkyl and $C_{1-10}$alkoxy being optionally substituted with 1-5 halo atoms up to perhalo;
  $R^2$ represents $C_{1-6}$alkyl, optionally substituted with 1-5 halo atoms up to perhalo;
  each $R^3$ represents H or is selected from the group consisting of halo; CN; a 5- membered heteroaryl ring containing 1-3 nitrogen atoms, 0-1 oxygen or sulfur atom, and optionally substituted with 1-2 $C_{1-4}$alkyl groups; $C_{1-10}$alkyl and $C_{1-10}$alkoxy, the alkyl portions of $C_{1-10}$alkyl and $C_{1-10}$alkoxy being optionally substituted with 1-5 halo atoms up to perhalo;
  each $R^4$ independently represents H or is selected from the group consisting of halo, OH, $C_{1-4}$alkyl and haloC$_{1-4}$alkyl;
  m represents 0, 1 or 2; such that when m represents 0 or 1, Z represents tetrazolyl; and when m represents 2, Z represents a member selected from the group consisting of $CO_2H$, $SO_3H$ and $C(O)NH_2$.

2. A compound in accordance with claim 1 or a pharmaceutically acceptable salt thereof wherein $R^2$ represents a member selected from the group consisting of: $C_{1-6}$alkyl, optionally substituted with 1-3 halo atoms.

3. A compound in accordance with claim 1 or a pharmaceutically acceptable salt thereof wherein $R^2$ represents $C_{2-5}$alkyl optionally substituted with 1-3 halo atoms.

4. A compound in accordance with claim 1 or a pharmaceutically acceptable salt thereof wherein $R^2$ is selected from the group consisting of ethyl, n-propyl, isopropyl, n-butyl, isobutyl, sec-butyl and 3-methylbutyl, each optionally substituted with 1-3 halo atoms selected from fluoro and chloro.

5. A compound in accordance with claim 1 or a pharmaceutically acceptable salt thereof wherein $R^2$ is selected from the group consisting of ethyl, n-propyl, n-butyl, $CH_2CH(CH_3)_2$, $CH_2CH_2CH(CH_3)_2$ and $CH_2CH_2CF_3$.

6. A compound in accordance with claim 1 or a pharmaceutically acceptable salt thereof wherein each $R^3$ represents H or is selected from the group consisting of halo, CN, $C_{1-6}$alkyl, $C_{1-6}$alkoxy, haloC$_{1-6}$alkyl, haloC$_{1-6}$alkoxy and a 5-membered heteroaryl ring containing 1-2 nitrogen atoms and 0-1 oxygen atom, said ring being optionally substituted with 1-2 $C_{1-4}$alkyl groups.

7. A compound in accordance with claim 1 or a pharmaceutically acceptable salt thereof wherein each $R^3$ represents H or is selected from the group consisting of halo which is selected from F, Cl and Br, CN, $C_{1-2}$alkyl, $C_{1-2}$alkoxy, haloC$_{1-2}$alkyl and haloC$_{1-2}$alkoxy wherein the halo portion of haloC$_{1-2}$alkyl and haloC$_{1-2}$alkoxy is selected from F and Cl, and a 5-membered heteroaryl ring containing 1-2 nitrogen atoms and 0-1 oxygen atom, said ring being optionally substituted with 1-2 $C_{1-4}$alkyl groups.

8. A compound in accordance with claim 1 or a pharmaceutically acceptable salt thereof wherein each $R^3$ represents H, F, Cl, Br, CN, $CH_3$, $OCH_3$, $OCH_2CH_3$, $CHF_2$, $CF_3$, $OCHF_2$, $OCF_3$ and a 5-membered heteroaryl ring containing 1-2 nitrogen atoms, 0-1 oxygen atom and being optionally substituted with 1 $C_{1-2}$alkyl group.

9. A compound in accordance with claim 1 or a pharmaceutically acceptable salt thereof wherein each $R^4$ represents H, halo selected from F and Cl, OH, $C_{1-2}$alkyl, and haloC$_{1-2}$alkyl wherein the halo portion of haloC$_{1-2}$alkyl is selected from F and Cl.

10. A compound in accordance with claim 1 or a pharmaceutically acceptable salt thereof wherein each $R^4$ represents H, F, $CH_3$ or OH.

11. A compound in accordance with claim 1 or a pharmaceutically acceptable salt thereof wherein m represents 0 or 1 and Z represents tetrazolyl.

12. A compound in accordance with claim 1 or a pharmaceutically acceptable salt thereof wherein m is 2 and Z represents $CO_2H$.

13. A compound in accordance with claim 1 or a pharmaceutically acceptable salt thereof wherein:
  each $R^1$ represents H or is selected from the group consisting of halo, $C_{1-6}$alkyl, $C_{1-6}$alkoxy, haloC$_{1-6}$alkyl and haloC$_{1-6}$alkoxy;
  $R^2$ represents $C_{1-6}$alkyl, optionally substituted with 1-3 halo atoms;
  each $R^3$ represents H or is selected from the group consisting of halo, CN, $C_{1-6}$alkyl, $C_{1-6}$alkoxy, haloC$_{1-6}$alkyl, haloC$_{1-6}$alkoxy and a 5-membered heteroaryl ring containing 1-2 nitrogen atoms and 0-1 oxygen atom, said ring being optionally substituted with 1-2 $C_{1-4}$alkyl groups;
  each $R^4$ represents H, halo selected from F and Cl, OH, $C_{1-2}$alkyl and haloC$_{1-2}$alkyl wherein the halo portion of haloC$_{1-2}$alkyl is selected from F and Cl; and
  m is 0 or 1 and Z is tetrazolyl, or m is 2 and Z represents $CO_2H$.

14. A compound in accordance with claim 1 selected from the group consisting of:

EXAMPLE 1

![Chemical structure of Example 1]

EXAMPLE 2

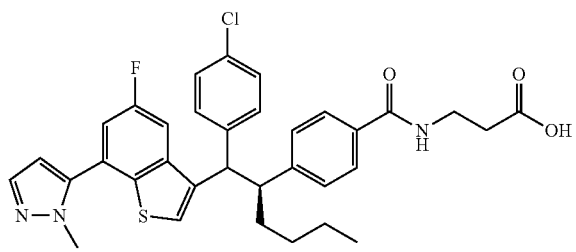

EXAMPLE 3

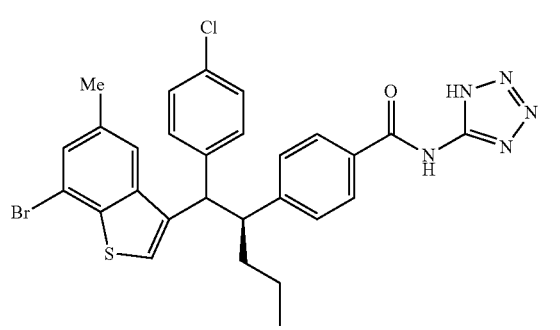

EXAMPLE 4

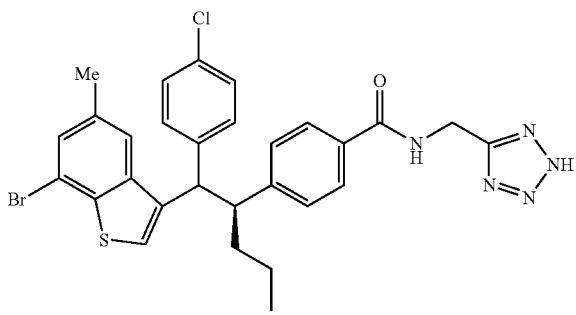

TABLE 1

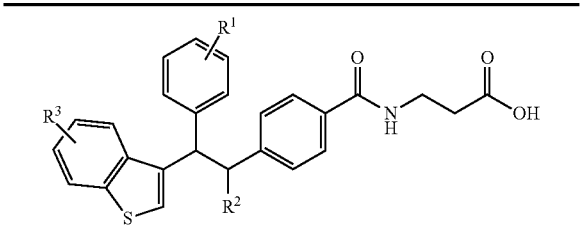

| EXAMPLE | R¹ | R² | R³ |
|---|---|---|---|
| 5 | 4-Cl | n-Pr | H |
| 6 | 4-Cl | n-Pr | 5-Cl, 7-Me |
| 7 | 4-Cl | n-Pr | 5-Cl, 7-Br |
| 8 | 4-Cl | n-Pr | 2-Me |
| 9 | 4-Cl | n-Pr | 5-F, 7-Cl |
| 10 | 4-OMe | n-Pr | H |
| 11 | 3,4-diCl | n-Pr | 5-Cl |
| 12 | 3,4-diCl | n-Pr | 5-Cl, 7-Br |
| 13 | 4-Cl | n-Pr | 5-F, 7-CN |
| 14 | 4-Cl | n-Pr | 5-Me, 7-CN |

TABLE 1-continued

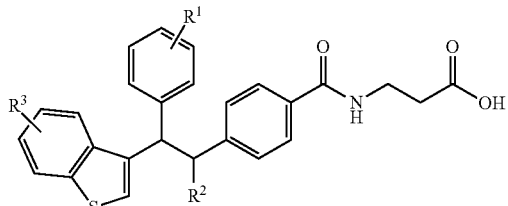

| EXAMPLE | R¹ | R² | R³ |
|---|---|---|---|
| 15 | 4-Cl | n-Pr | 5-CF₃, 7-CN |
| 16 | 4-Cl | n-Pr | 5,6-diF, 7-CN |
| 17 | 4-Cl | n-Pr | 4,5-diF, 7-CN |
| 18 | 4-Cl | n-Pr | 2-Me, 5-F, 7-CN |
| 19 | 4-Cl | n-Pr | 2-Me, 5-Cl, 7-CN |
| 20 | 3,5-diF | n-Pr | 5-CF₃, 7-CN |
| 21 | 3,4-diCl | n-Pr | 5-Cl, 7-CN |
| 22 | 4-OCF₃ | n-Pr | 5-F, 7-CN |
| 23 | 4-OCF₃ | n-Pr | 5-Me, 7-CN |
| 24 | 4-OCF₃ | n-Pr | 5-CF₃, 7-CN |
| 25 | 4-OCF₃ | n-Pr | 5-Cl, 7-CN |
| 26 | 4-OCF₃ | n-Pr | 5,6-diF, 7-CN |
| 27 | 4-Cl | —CH₂CH₂CF₃ | 5-Cl, 7-CN |
| 28 | 4-Cl | —CH₂CH₂CF₃ | 5-Me, 7-CN |
| 29 | 4-Cl | n-Bu | 5-Cl, 7-CN |
| 30 | 4-Cl | n-Bu | 5-F, 7-CN |
| 31 | 4-Cl | n-Bu | 5-CF₃, 7-CN |
| 32 | 4-Cl | —CH₂CH(CH₃)₂ | 5-Cl, 7-CN |
| 33 | 4-Cl | —CH₂CH(CH₃)₂ | 5-F, 7-CN |
| 34 | 4-Cl | Et | 5-Cl, 7-CN |
| 35 | 4-Cl | n-Pr | 5-Cl, 7- 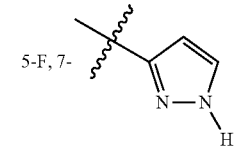 [SMILES: *c1cc[nH]n1] |
| 36 | 4-OCF₃ | n-Pr | 5-F, 7- 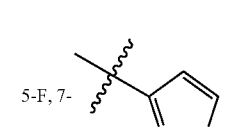 |
| 37 | 4-Cl | n-Bu | 5-F, 7- 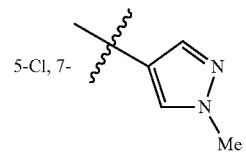 |
| 38 | 4-Cl | n-Pr | 5-Cl, 7- 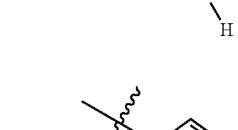 |

TABLE 2

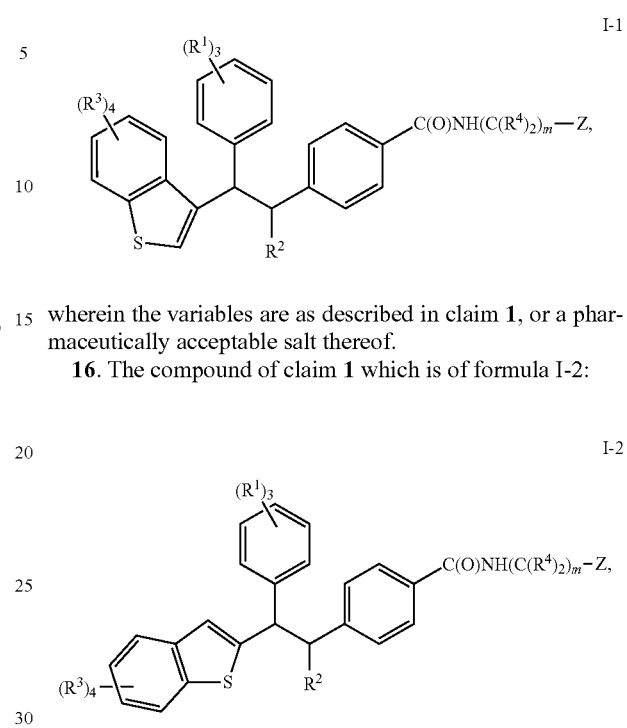

| EXAMPLE | Y |
|---|---|
| 39 | (S)-CH(CH₃)CH(OH)C(O)OH structure |
| 40 | CH₂C(F)₂C(O)OH structure |
| 41 | CH₂CH(Me)C(O)OH structure |
| 42 | CH₂CH(Me)CH₂C(O)OH structure |
| 43 | CH₂CH₂S(O)₂OH structure |
| 44 | CH₂CH₂C(O)NH₂ structure |

TABLE 3

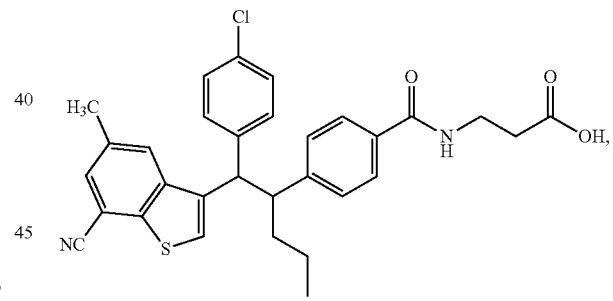

| EXAMPLE | $R^1$ | $R^2$ | $R^3$ |
|---|---|---|---|
| 45 | 4-Cl | n-Pr | H |
| 46 | 4-Cl | n-Pr | 5-Cl |
| 47 | 4-Cl | n-Pr | 7-Cl |
| 48 | 4-OMe | n-Pr | 5-Cl | or a pharmaceutically acceptable salt thereof.

15. The compound of claim 1 which is of formula I-1:

I-1 wherein the variables are as described in claim 1, or a pharmaceutically acceptable salt thereof.

16. The compound of claim 1 which is of formula I-2:

I-2 wherein the variables are as described in claim 1, or a pharmaceutically acceptable salt thereof.

17. The compound of claim 1 which is:

or a pharmaceutically acceptable salt thereof.

18. A pharmaceutical composition comprising a compound in accordance with claim 1 or a pharmaceutically acceptable salt thereof in combination with a pharmaceutically acceptable carrier.

19. A pharmaceutical composition in accordance with claim 18 further comprised of a member selected from the group consisting of: simvastatin, mevastatin, ezetimibe, atorvastatin, metformin, sibutramine, orlistat, Qnexa, topiramate, naltrexone, bupriopion, phentermine, losartan, hydrochlorothiazide, buformin, phenformin, troglitazone, pioglitazone, rosiglitazone, insulin, somatostatin, voglibose, miglitol, acarbose, sitagliptin, vildagliptin, saxagliptin, alogliptin, acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide, repaglinide, rimonabant and taranabant.

20. A method of treating type 2 diabetes mellitus in a mammalian patient in need of such treatment comprising administering to said patient a compound in accordance with claim 1 or a pharmaceutically acceptable salt thereof in an amount that is effective to treat said type 2 diabetes mellitus.

* * * * *